United States Patent
Zhang et al.

(10) Patent No.: US 11,994,473 B2
(45) Date of Patent: May 28, 2024

(54) PULSE PICKING APPARATUSES AND METHODS FOR NONLINEAR OPTICAL MICROSCOPY

(71) Applicant: Purdue Research Foundation, West Lafayette, IN (US)

(72) Inventors: Chi Zhang, West Lafayette, IN (US); Matthew Graham Clark, Lafayette, IN (US)

(73) Assignee: PURDUE RESEARCH FOUNDATION, West Lafayette, IN (US)

(*) Notice: Subject to any disclaimer, the term of this patent is extended or adjusted under 35 U.S.C. 154(b) by 0 days.

(21) Appl. No.: 17/935,563

(22) Filed: Sep. 26, 2022

(65) Prior Publication Data

US 2023/0129700 A1    Apr. 27, 2023

Related U.S. Application Data

(60) Provisional application No. 63/261,592, filed on Sep. 24, 2021.

(51) Int. Cl.
*G01J 3/44* (2006.01)
*G01N 21/21* (2006.01)
(Continued)

(52) U.S. Cl.
CPC .......... *G01N 21/65* (2013.01); *G01N 21/21* (2013.01); *G01N 33/4833* (2013.01);
(Continued)

(58) Field of Classification Search
CPC ........ G01N 21/65; G01N 21/64; G01N 21/21; G01J 3/02; G01J 3/28; G01J 3/14; G01J 3/18; G01J 3/44
See application file for complete search history.

(56) References Cited

U.S. PATENT DOCUMENTS 5,867,305 A * 2/1999 Waarts ................ H01S 3/06758
                                                              372/6
6,134,050 A * 10/2000 Conemac ............. G02B 27/145
                                                              359/583

(Continued)

OTHER PUBLICATIONS

Dan Fu, et al; "Hyperspectral Imaging with Stimulated Raman Scattering by Chirped Femtosecond Lasers", The Journal of Physical Chemistry B; 2013, 117, 4634-4640, Dec. 20, 2012.

(Continued)

*Primary Examiner* — Abdullahi Nur

(57) ABSTRACT

Embodiments of the present disclosure are disclosed for enhancing resolution for nonlinear optical microscopy. Embodiments include pulse picking using a modulator, such as an acousto-optic modulator, that is optionally controlled by a function generator or a frequency divider. Some embodiments spatially overlap two laser beams prior to the modulator, and still additional embodiments include separating the $1^{st}$ diffraction order of the modulated laser output of the acousto-optic modulator and directing the $1^{st}$ diffraction order to a microscope. Some embodiments chirp a spatially overlapped laser beam with one pulse rate to a spatially overlapped laser beam with a higher pulse rate, while still additional embodiments utilize a coherent Raman scattering microscope.

20 Claims, 21 Drawing Sheets

(51) Int. Cl.
  *G01N 21/65*      (2006.01)
  *G01N 33/483*     (2006.01)
  *G02B 21/00*      (2006.01)
(52) U.S. Cl.
  CPC ..... *G02B 21/0032* (2013.01); *G02B 21/0048* (2013.01); *G01N 2021/653* (2013.01); *G01N 2201/06113* (2013.01)

(56) References Cited

U.S. PATENT DOCUMENTS

| | | | | |
|---|---|---|---|---|
| 2002/0067490 | A1* | 6/2002 | Okawauchi | G03F 7/70633 356/614 |
| 2004/0134894 | A1* | 7/2004 | Gu | B23K 26/0736 257/E23.15 |
| 2011/0109958 | A1* | 5/2011 | Yokoi | G02B 21/06 359/385 |
| 2019/0360937 | A1* | 11/2019 | Liao | G01N 21/65 |

OTHER PUBLICATIONS

Erik M. Vartiainen; "Phase retrieval approach for coherent anti-Stokes Raman scattering spectrum analysis", J. Opt. Soc. Am. B; vol. 9, No. 8, Aug. 1992; 6 pages.

Yuexin Liu, et al; "Broadband CARS spectral phase retrieval using a time-domain Kramers—Kronig transform", Optics Letters, May 1, 2009, vol. 34, No. 9; 3 pages.

Weili Hong; "In situ Detection of a Single Bacterium in Complex Environment by Hyperspectral CARS Imaging", Chemistry Select, Mar. 2016, 513-517.

Kai-Chih Huang; "Multiplex Stimulated Raman Scattering Imaging Cytometry Reveals Lipid-Rich Protrusions in Cancer Cells under Stress Condition", iScience 23, 100953, Mar. 27, 2020; 41 pages.

Petra Schwille; "Molecular Dynamics in Living Cells Observed by Fluorescence Correlation Spectroscopy with One- and Two-Photon Excitation", Biophysical Journal vol. 77 Oct. 1999 2251-2265.

Haohua Tu, et al; "Stain-free histopathology by programmable supercontinuum pulses", Nature Photonics | vol. 10 | Aug. 2016 4 pages.

* cited by examiner

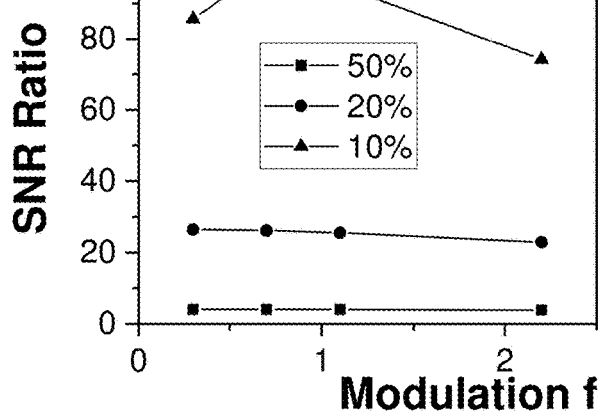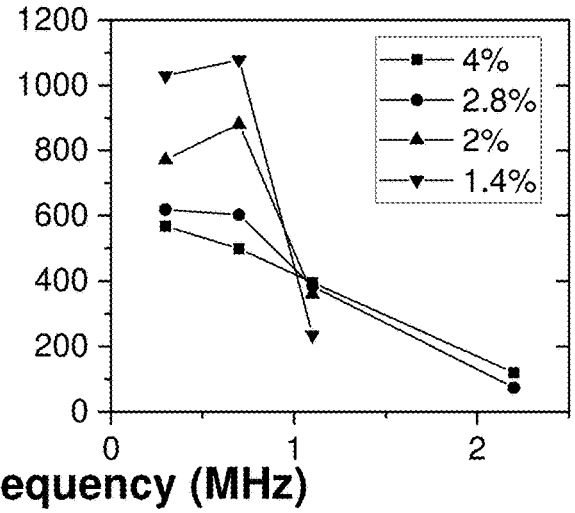
Fig. 5A              Fig. 5B
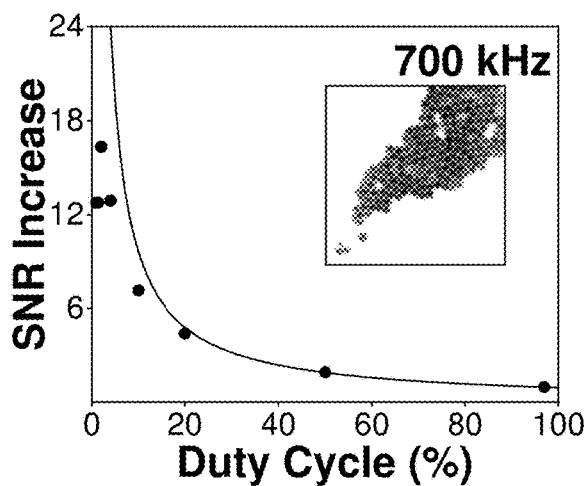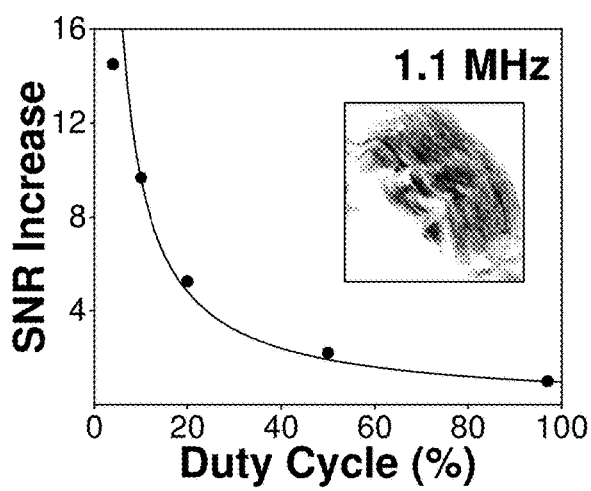
Fig. 6              Fig. 7

97%  20%  10%

4%  1.44%

Chemical Map

FCARS
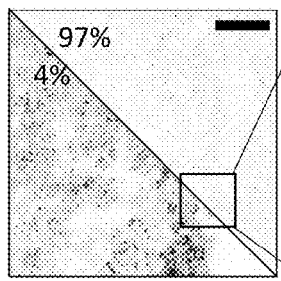 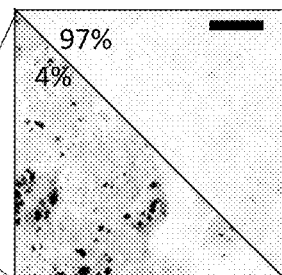
ECARS
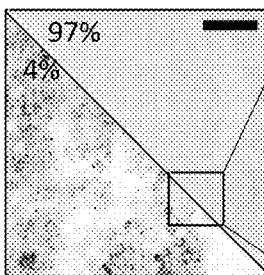 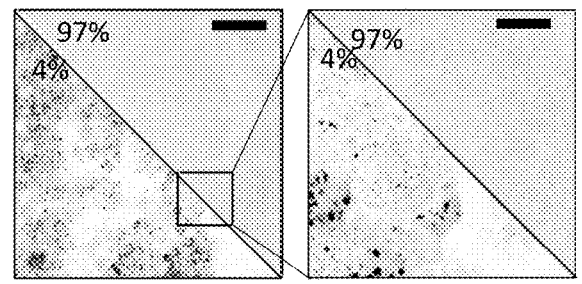
Fig. 15A  Fig. 15B  Fig. 16A  Fig. 16B
TPEF 450 nm
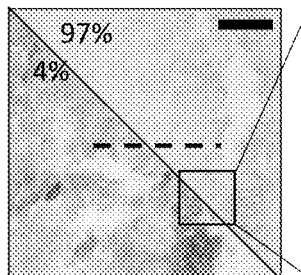 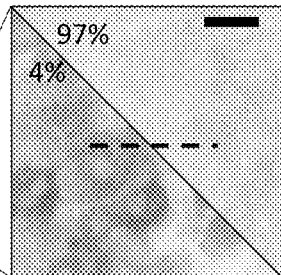
TPEF 570 nm
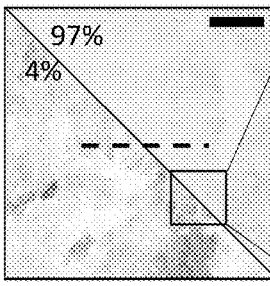 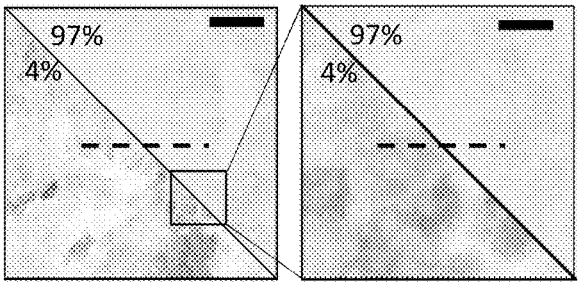
Fig. 17A  Fig. 17B  Fig. 18A  Fig. 18B

ECARS

SHG

97% duty cycle picosecond pulses, pump:
60 mW (227W), Stokes: 40 mW (286W)

5% duty cycle picosecond pulses, pump:
7.5 mW (551 W), Stokes 5 mW (694 W)

1.4% duty cycle picosecond pulses, pump:
6 mW (1576 W), Stokes: 4 mW (1984 W)

Different peak/average power,
Same signal level and contrast 50 frames of CARS images 97% picosecond
Average: 60 mW, 40 mW
Peak: 227 W, 286 W 1.4% picosecond
Average: 6 mW, 4 mW
Peak: 227 W, 1984 W Tracing the trajectories Quantitative analysis
and comparison Maximum displacement

PULSE PICKING APPARATUSES AND METHODS FOR NONLINEAR OPTICAL MICROSCOPY

This application claims the benefit of U.S. Provisional Application No. 63/261,592, filed Sep. 24, 2021, the entirety of which is hereby incorporated herein by reference.

FIELD

Embodiments of this disclosure relate generally to nonlinear optical microscopy, and to apparatuses and methods for enhancing the sensitivity of nonlinear optical microscopy.

BACKGROUND

When a material is illuminated by light, for example laser light, the photons are generally scattered. Most of the scattered photons have the same energy after being scattered as they had before being scattered. However, some of the photons have different energy, usually lower but sometimes higher, after being scattered because the material changes energy, usually absorbing but sometimes losing energy, respectively, due to the scattering of photons. The scattering of photons that change their energy after illuminating matter is commonly referred to as Raman scattering. The number of photons that change their energy level when scattered is substantially less than the number of photons that do not change their energy level. Because the material being illuminated changes energy, Raman scattering has been used for gaining insight into the material being illuminated.

Chemical analysis of biological samples can assist in understanding biofunctions and diagnosing pathological transitions of diseases. Example areas of interest include label-free acquisition of chemical information in living samples, which may be addressed using nonlinear optical microscopy techniques to achieve label-free mapping of chemicals. Example techniques include use of a single laser-scanning microscope for multimodal imaging. In general, multiphoton excitation fluorescence (MPEF) and second harmonic generation (SHG) use femtosecond (fs) laser pulses for signal excitation. Coherent Raman scattering (CRS), however, typically utilizes picosecond (ps) laser pulses to achieve high spectral resolution. Hyperspectral CRS microscopy applies either two narrow-band ps laser pulses, combined narrow and broadband laser pulses, or spectrally chirped broadband laser pulses. The different requirement makes hyperspectral CRS less compatible with MPEF and SHG. However, problems exist with these known techniques, such as inducing phototoxicity in biological samples to integrate all modalities. One manner in which to integrate CRS with MPEF and SHG is by using pulse picking. However, current pulse picking methods cannot be applied to two laser wavelengths simultaneously and/or require a very high amount of power (approximately 5000 V) to operate.

Known optical processes for imaging include multiphoton excitation fluorescence (MPEF), second harmonic generation (SHG), and coherent Raman scattering (CRS). MPEF is frequently used for probing intrinsic fluorophores such as nicotinamide adenine dinucleotide (NADH) and flavin adenine dinucleotide (FAD). SHG is frequently used for noncentrosymmetric compositions such as collagen and elastin. And, CRS processes, including both coherent anti-Stokes Raman scattering (CARS) and stimulated Raman scattering (SRS), harness molecular vibrational transitions excited by an ultrafast laser It was realized by the inventors of the current disclosure that problems exist with current techniques for examining materials, especially living tissue, and known techniques (such as Raman scattering) have difficulties and that improvements in imaging are needed.

Embodiments disclosed herein utilize acousto-optics properties of pulse-picking nonlinear optical microscopy and can simultaneously work for two laser wavelengths. Various embodiments integrate MPEF, SHG, and hyperspectral CARS modalities.

Certain preferred features of the present disclosure address these and other needs and provide other important advantages.

SUMMARY

Embodiments of the present disclosure provide improved pulse-picking apparatuses and methods for nonlinear optical microscopy.

Additional embodiments provide pulse-picking apparatuses and methods for coherent anti-Stokes Raman scattering microscopy, such as for highly sensitive chemical imaging.

Embodiments of the present disclosure include pulse-picking multimodal nonlinear optical (PPMNO) microscopes, an example of which is a pulse-picking coherent anti-Stokes Raman scattering (PPCARS) microscope.

Embodiments of the present disclosure utilize pulse picking systems and methods as disclosed herein with coherent Raman scattering (CRS, which includes coherent anti-Stokes Raman scattering (CARS), forward coherent anti-Stokes Raman scattering (also known as forward CARS, or FCARS), epi-coherent anti-Stokes Raman scattering (also known as epi-CARS, or ECARS) and hyperspectral coherent anti-Stokes Raman scattering (also known as hyperspectral CARS) microscopy as well as other types of microscopy, for example, second harmonic generation (also known as SHG) microscopy and multiphoton excitation fluorescence (also known as MPEF, (which includes two-photon excited fluorescence (also known as TPEF)) microscopy.

Embodiments of the present disclosure provide a pulse picking technology that can significantly increase the sensitivity of Raman microscopy, and in some embodiments coherent anti-Stokes Raman scattering (CARS) microscopy and/or other nonlinear optical imaging modalities (such as multiphoton excitation fluorescence and/or second harmonic generation).

Embodiments of the present disclosure utilize a pulse picking approach based on an acousto-optic modulator (AOM) for simultaneous MPEF, SHG, and hyperspectral CARS imaging. Some embodiments apply one laser beam at the Bragg angle error condition and collinearly combine the pump and Stokes beams at the $1^{st}$ order of the AOM. This pulse picking nonlinear optical microscope can provide flexible control of the optimal number of pulses at each pixel to maximize sensitivity and minimize photo-perturbation to biological samples and can enable integration of hyperspectral CARS, MPEF, and SHG modalities using the same laser source.

Embodiments utilize spectral focusing, which can achieve high spectral resolution for hyperspectral CARS and good sensitivity for MPEF and SHG. Moreover, embodiments utilizing the pulse picking method promote evaluation of the phototoxicity of laser pulses at different average and peak power levels, which can be used to optimize the laser pulses for, for example, multimodal CARS, MPEF, and SHG imaging.

Embodiments utilize nonlinear optical microscopy techniques to map chemical compositions in biological samples in a label-free manner. Example techniques used in example embodiments include multiphoton excitation fluorescence (MPEF), second harmonic generation (SHG) and coherent Raman scattering (CRS) microscopy.

Femtosecond lasers are typically used for MPEF and SHG modalities due to the requirement of high peak power for excitation, while picosecond lasers are preferred for CRS due to the need for high spectral resolution. The inventors realized that it is challenging to integrate CRS with MPEF and SHG for chemical imaging. However, embodiments of the present disclosure utilize a pulse picking strategy (such as, for example, utilizing an acousto-optic modulator) where the duty cycle of the laser pulse train can be programmed, significantly increasing the pulse peak power at low input average power. This approach can offer strong enhancement of nonlinear optical signals and can make hyperspectral coherent anti-Stokes Raman scattering (CARS) microscopy compatible with MPEF and SHG for multimodal imaging at low laser average power. Embodiments of the present disclosure also utilize the pulse picking methodologies to evaluate and compare the phototoxicity of laser pulses at different average and peak power levels. The photo-perturbations to biological samples can be evaluated by embodiments of the present disclosure using cellular dynamics and morphology changes, allowing the selection of optimal laser power range for the best sensitivity and minimal phototoxicity Embodiments of the present disclosure include integration of imaging modalities without increasing, and possibly decreasing, laser phototoxicity.

Embodiments of the present disclosure include pulse picking apparatuses and methods that increase the sensitivity of multimodal nonlinear optical imaging modalities including hyperspectral CARS, TPEF, and SHG. Various embodiments utilize a function-generator-controlled AOM and apply one of the two or more excitation beams at a Bragg angle error condition. The pump and Stokes beams can be combined at the $1^{st}$ order of AOM in some embodiments. By reducing the duty cycle of the laser beams, improvements in the signal-to-noise ratio (SNR) sensitivities of CARS, TPEF, and SHG allow for reduced average input power. Pulse picking apparatuses and methods of the present disclosure can achieve better sensitivity enhancement for higher-order nonlinear optical processes. While maintaining the peak power at a safe range, embodiments of the present disclosure allow an increase in the peak power and provide improved image contrast and less phototoxicity.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein does not necessarily address every object described herein, and each embodiment does not necessarily include each feature described. Other forms, embodiments, objects, advantages, benefits, features, and aspects of the present disclosure will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions or may have been created from scaled drawings. However, such dimensions, or the relative scaling within a figure, are by way of example, and not to be construed as limiting.

FIGS. 5A and 5B are graphical representations depicting CARS SNR increases versus modulation frequency at different duty cycles resulting from obtained from an example PPCARS microscope as represented by FIG. 1.

FIG. 6 is a graphical representation depicting two-photon excited fluorescence (TPEF) SNR increases versus duty cycle at 700 kHz modulation frequency obtained from an example PPCARS microscope as represented by FIG. 1. Dots are experimental data, the curve is the theoretical function of 1/D and D is the duty cycle. The image inset shows a TPEFF image of fluorescent microparticles from which SNR values were derived.

FIG. 7 is a graphical representation depicting second harmonic generation (SHG) SNR increases versus duty cycle at 1.1 MHz modulation frequency obtained from an example PPCARS microscope as represented by FIG. 1. Dots are experimental data, the curve is the theoretical function of 1/D and D is the duty cycle. The image inset shows a mouse tail tendon specimen from which SNR values were derived.

FIG. 8A is a graphical representation depicting a CARS spectra of methanol and DMSO in the C—H region obtained from an example PPCARS microscope as represented by FIG. 1.

FIG. 8B is a graphical representation depicting a plot of CARS signal intensity versus DMSO concentration (%) in $D_2O$ obtained from an example PPCARS microscope as represented by FIG. 1. Dots are experimental values and the curve is a quadratic fitting of experimental results.

FIG. 8C is a graphical representation depicting a phase-retrieved Raman spectra of 1%-0.05% DMSO in $D_2O$ obtained from an example PPCARS microscope as represented by FIG. 1.

FIG. 8D is a graphical representation depicting a peak fitting of phase-retrieved Raman spectrum of 1% DMSO in $D_2O$ obtained from an example PPCARS microscope as represented by FIG. 1.

FIG. 8E is a graphical representation depicting a fingerprint region retrieved Raman spectra of 1 µm PS (solid line) and polymethyl methacrylate (PMMA) beads (dashed line) from PPCARS images obtained from an example PPCARS microscope as represented by FIG. 1.

FIG. 8F is a graphical representation depicting a spectral peak fitting of PS 1583 $cm^{-1}$ and 1602 $cm^{-1}$ stretching obtained from an example PPCARS microscope as represented by FIG. 1.

FIG. 8G is a graphical representation depicting a CARS image of a mixture of 1 µm PS and PMMA beads at a 97% duty cycle and a 700 kHz modulation frequency obtained from an example PPCARS microscope as represented by FIG. 1.

FIG. 8H is a graphical representation depicting CARS images of the mixture of 1 µm PS and PMMA beads from FIG. 8G, but at a 4% duty cycle and a 700 kHz modulation frequency obtained from an example PPCARS microscope as represented by FIG. 1.

FIG. 8I is a graphical representation depicting spectral-phasor-generated chemical map of mixed beads (PS and PMMA) using the fingerprint hyperspectral PPCARS images obtained from an example PPCARS microscope as represented by FIG. 1. The power at the samples are: 5.2 mW pump and 6.2 mW Stokes for the C—H imaging; and 13.7 mW pump and 6.2 mW Stokes for the fingerprint imaging.

FIGS. 9A-14 are produced imaging and chemical segmentation of cells obtained from an example PPCARS microscope as represented by FIG. 1. Power at the sample for FIGS. 9A-11C are pump 10.8 mW and Stokes 5.0 mW, with a pixel dwell time of 10 µs. Power at the sample for FIGS. 12-14 are pump 2.0 mW and Stokes 3.7 mW, with a pixel dwell time of 10 µs. The scale bars are 10 µm.

FIGS. 9A, 9B, 9C, 9D and 9E are forward coherent anti-Stokes Raman scattering (also known as forward CARS, or FCARS) images of Mia PaCa-2 cells at 97% (FIG. 9A), 20% (FIG. 9B), 10% (FIG. 9C), 4% (FIG. 9D), and 1.4% (FIG. 9E) duty cycles at 700 kHz modulation frequency obtained from an example PPCARS microscope as represented by FIG. 1.

FIGS. 10A, 10B, 10O, 10D and 10E are epi-coherent anti-Stokes Raman scattering (also known as epi-CARS, or ECARS) images of Mia PaCa-2 cells at 97% (FIG. 10A), 20% (FIG. 10B), 10% (FIG. 10O), 4% (FIG. 10D), and 1.44% (FIG. 10E) duty cycles at 700 kHz modulation frequency obtained from an example PPCARS microscope as represented by FIG. 1.

FIGS. 11A, 11B and 11O are line profile plots comparing FCARS (top) and ECARS (bottom) images at 97% (FIG. 11A), 10% (FIG. 11B), and 1.44% (FIG. 11C) duty cycles along the dashed white lines depicted in FIGS. 9A and 10A, FIGS. 9C and 10O, and FIGS. 9E and 10E, respectively.

FIG. 13 is a chemical map of Mia PaCa-2 cells comprised of the cytosol, ER, nuclei, and LD compositions of FIGS. 12A, 12B, 12C, 12D and 12E.

FIG. 14 is a graphical representation of phase-retrieved Raman spectra from the four cellular components of FIGS. 12A, 12B, 12C, 12D and 12E. The average power at the samples for all cell images was: pump 2.0 mW, Stokes 3.7 mW, and pixel dwell time 10 µs.

FIGS. 15A-22B are multimodal imaging of mouse tissue samples at high and low duty cycles according to embodiments of the present disclosure. Power at the samples: pump 18.0 mW, Stokes 12.6 mW for CARS and TPEF; 1.4 mW 1045 nm for SHG. Pixel dwell time: 10 µs. Scale bars, 50 µm and 10 µm for left and right images, respectively, for each panel.

FIGS. 15A and 15B depict a side-by-side comparison of 4% and 97% duty cycles with the same average input power for FCARS imaging of a mouse liver sample in FIG. 15A with an enlarged depiction of the boxed region FIG. 15A represented in FIG. 15B.

FIGS. 16A and 16B depict a side-by-side comparison of 4% and 97% duty cycles with the same average input power for ECARS imaging of a mouse liver sample in FIG. 16A with an enlarged depiction of the boxed region FIG. 16A represented in FIG. 16B.

FIGS. 17A and 17B depict a side-by-side comparison of 4% and 97% duty cycles with the same average input power for TPEF 450 nm imaging of a mouse liver sample in FIG. 17A with an enlarged depiction of the boxed region FIG. 17A represented in FIG. 17B.

FIGS. 18A and 18B depict a side-by-side comparison of 4% and 97% duty cycles with the same average input power for TPEF 570 nm imaging of a mouse liver sample in FIG. 18A with an enlarged depiction of the boxed region FIG. 18A represented in FIG. 18B.

FIG. 19A is from FCARS using 97% duty cycle. FIG. 19B is from ECARS using 97% duty cycle. FIG. 19C is from FCARS using 4% duty cycle. FIG. 19D is from ECARS using 4% duty cycle FIG. 20A is from TPEF 450 nm using 97% duty cycle. FIG. 20B is from TPEF 570 nm using 97% duty cycle. FIG. 20C is from TPEF 450 nm using 4% duty cycle. FIG. 20D is from TPEF 570 nm using 4% duty cycle.

FIGS. 22A and 22B depict a comparison of 97% (FIG. 22A) and 4% (FIG. 22B) duty cycles for SHG imaging of mouse tail tendons.

FIGS. 23A-25E depict the results of phototoxicity evaluations and the evolution of photodamage induced by different average power (1-60 mW) and peak power (227-12,200 W).

FIGS. 23A, 23B, 23C, 23D, and 23E depict time-lapse imaging of a mouse spleen tissue sample at a 97% duty cycle of picosecond pulses with a pump of 60 mW (227 W) and a Stokes of 40 mW (286 W). The scale bar is 10 μm.

FIGS. 25A, 25B, 25C, 25D, and 25E depict time-lapse imaging of a mouse spleen tissue sample at a 1.4% duty cycle of picosecond pulses with a pump of 6 mW (1576 W) and a Stokes of 4 mW (1984 W). The scale bar is 10 μm.

FIG. 28D is a comparison of maximum displacement median values of the lognormal fitting results from FIGS. 28A, 28B and 28C.

DETAILED DESCRIPTION OF THE ILLUSTRATED EMBODIMENTS

Figure 1:
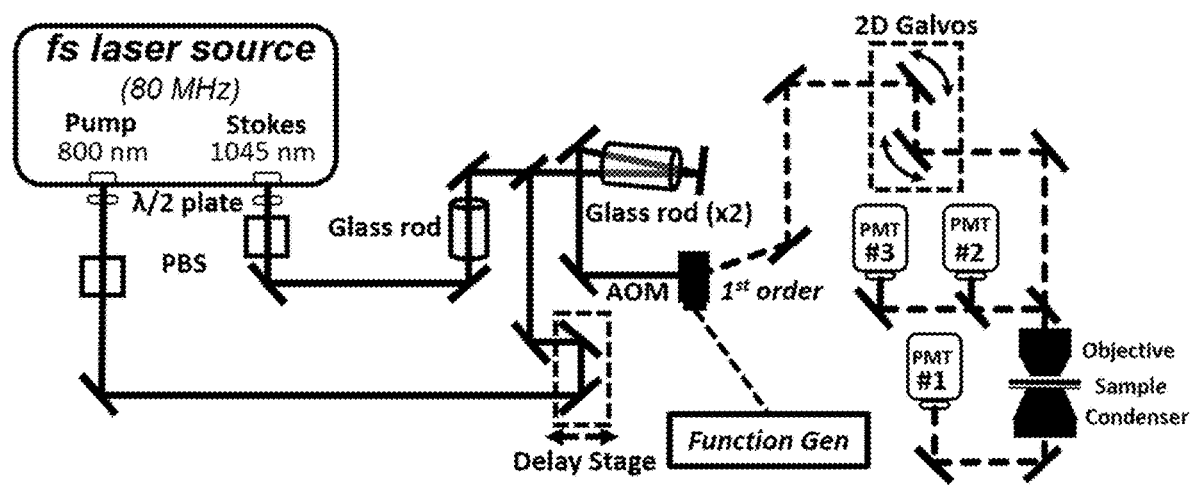
FIG. 1 is a schematic representation of a microscope, which may be referred to as a pulse-picking multimodal nonlinear optical (PPMNO) microscope, an example of which is a pulse-picking coherent anti-Stokes Raman scattering (PPCARS) microscope, according to one embodiment of the present disclosure. The microscope includes a beam splitter (for example, a polarization beam splitter (PBS)), a modulator (for example, an acousto-optic modulator (AOM)), a photomultiplier (for example, a photomultiplier tube (PMT)), a laser beam combiner (for example, a dichroic mirror (DM)), and a wave plate (for example, a half-wave plate (HWP)).

For the purposes of promoting an understanding of the principles of the disclosure, reference will now be made to one or more embodiments, which may or may not be illustrated in the drawings, and specific language will be used to describe the same. It will nevertheless be understood that no limitation of the scope of the disclosure is thereby intended; any alterations and further modifications of the described or illustrated embodiments, and any further applications of the principles of the disclosure as illustrated herein are contemplated as would normally occur to one skilled in the art to which the disclosure relates. At least one embodiment of the disclosure is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to benefits or advantages provided by some embodiments, other embodiments may not include those same benefits or advantages, or may include different benefits or advantages. Any benefits or advantages described herein are not to be construed as limiting to any of the claims.

Likewise, there may be discussion with regards to "objects" associated with some embodiments of the present invention, it is understood that yet other embodiments may not be associated with those same objects, or may include yet different objects. Any advantages, objects, or similar words used herein are not to be construed as limiting to any of the claims. The usage of words indicating preference, such as "preferably," refers to features and aspects that are present in at least one embodiment, but which are optional for some embodiments.

Specific quantities (spatial dimensions, temperatures, pressures, times, force, resistance, current, voltage, concentrations, wavelengths, frequencies, heat transfer coefficients, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

Many nonlinear optical microscopy technologies use high repetition rate laser sources (for example, repetition rates of 70-100 MHz) for signal excitation. Reducing the repetition rate can generate higher pulse energy at the same input laser power, which can result in improved sensitivity for nonlinear optical imaging. Some pulse picking methods have been developed for nonlinear optical microscopy and can allow a reduction in laser repetition rates for a single laser beam. However, embodiments of the present disclosure provide the ability to simultaneously pick pulses from two or more laser beams (with the beams optionally at different frequencies) using, for example, an acousto-optic modulator. The embodiments are particularly useful for improving the sensitivity of microscopy technologies that require two frequencies for excitation, such as coherent anti-Stokes Raman scattering microscopy. The pulse picking devices of embodiments of this disclosure can also be very cost-effective and do not require the high voltage power supplies required with other techniques, such as those required for systems using Pockels cells. Embodiments of the present disclosure are able to significantly improve the sensitivity of various types of microscopy (such as, for example, coherent anti-Stokes Raman scattering microscopy and other nonlinear optical modalities such as harmonic generation and multiphoton excitation fluorescence) without increasing phototoxicity and are widely applicable to various types of nonlinear optical imaging systems (for example, coherent Raman scattering microscopy).

A widely used light source for nonlinear optical microscopy is a high-repetition-rate femtosecond or picosecond laser. Using as an example an 80 MHz laser repetition rate and a 10 μs pixel dwell time, there are 800 pulses on each image pixel. Since nonlinear optical signals are usually proportional to the square or cubic of laser peak power, reducing the number of pulses at each pixel with higher pulse energy can improve sensitivity while maintaining the same average input power. Embodiments of the present disclosure utilize a pulse picking technology to reduce the duty cycle of high repetition rate lasers for high sensitivity nonlinear optical microscopy.

Embodiments of the present disclosure include pulse picking apparatuses and methods for sensitivity improvement of Raman scattering microscopy, including coherent anti-Stokes Raman scattering (CARS) microscopy, two-photon excited autofluorescence (TPEF) Raman microscopy, and/or Second harmonic generation (SHG) Raman microscopy.

Embodiments of the present disclosure include pulse-picking multimodal nonlinear optical (PPMNO) microscopes (an example of which is a pulse-picking coherent anti-Stokes Raman scattering (PPCARS) microscope) as described herein with average power from 2 mW to 30 mW and peak power from 50 W to 4000 W. Further embodiments include pulse-picking multimodal nonlinear optical (PPMNO) microscopes as described herein with an average power of approximately 24 mW and peak power of approximately 3600 W. In these embodiments the duty cycle is chosen to achieve the desired average and peak power ranges. In contrast, for non-pulse picking microscopes, the average and/or peak power must be increased to obtain comparable image quality, but the increased power will result in increased phototoxicity. It is noted that most of the experimental data and analysis described herein were achieved using a PPCARS microscope embodiment, while the techniques, data, and analysis apply to other embodiments of pulse-picking multimodal nonlinear optical (PPMNO) microscopes.

A pulse-picking multimodal nonlinear optical (PPMNO) microscope according to one embodiment of the present disclosure is illustrated in FIG. 1. The illustrated embodiment includes a laser (for example, a femtosecond (fs) laser) with synchronized dual outputs, such as one operating as a Stokes beam (for example, one with a fixed wavelength, such as at 1045 nm) and the other as a pump beam (for example, one with a tunable wavelength, such as from 690-1300 nm). The two beams may be combined and/or chirped by multiple glass rods (for example, SF-57 glass rods) for spectral focusing. Before the microscope, the Stokes pulse may be chirped (such as to 1.8 picoseconds (ps)) while the pump pulse is chirped (such as to 3.4 µs). The two pulses can also have the same chirp rate, which can help ensure optimal spectral resolution. The ratio of pulse durations may match the ratio of spectral widths, which should assist with ensuring optimal spectral resolution using spectral focusing. The combined beams may be sent to a modulator (for example, an acousto-optic modulator (AOM)) that may be controlled by a function generator or a frequency divider. Square waves, such as square waves with tunable duty cycles (for example, from 1.4% to 97%) at various modulation frequencies may be sent to the AOM for pulse picking.

The $1^{st}$ order AOM output may be directed to a microscope, such as a laser-scanning microscope (for example, an upright laser-scanning microscope with two photomultiplier tubes (PMTs)), one in the epi-direction and one in the forward direction. As shown in FIG. 1, PMT1 is for forward coherent anti-Stokes Raman scattering (also known as forward CARS, or FCARS) detection, PMT2 is for the acquisition of two-photon excitation fluorescence (TPEF) signals (such as signals at 450 nm), and PMTS is for collection of either TPEF signals (such as signals at 570 nm), SHG signals, or epi-coherent anti-Stokes Raman scattering (also known as epi-CARS, or ECARS) signals.

In one example embodiment, the $1^{st}$ diffraction order from the AOM is used for imaging instead of the $0^{th}$ order since the $1^{st}$ order can completely shut off the laser beam at the 'time-off' periods, increasing (and potentially maximizing) the nonlinear optical signal generation at a fixed input average power. However, the AOM Bragg angles for the pump and Stokes wavelengths may be different. To assist with beam overlap along the $1^{st}$ order of diffraction, one of the beams can be slightly misaligned from the perfect Bragg angle. The AOM beam separation angle between the $0^{th}$ and $1^{st}$ orders, regardless of the incidence angle, is represented by Equation 1:

$$\theta_s = \frac{\lambda f}{V}, \tag{1}$$

where $\lambda$ is the beam wavelength, f is the acoustic frequency, and V is the acoustic velocity. The Bragg angle is half of the separation angle is represented by Equation 2:

$$\theta_B = \frac{\lambda f}{2V}. \tag{2}$$

Figure 2:
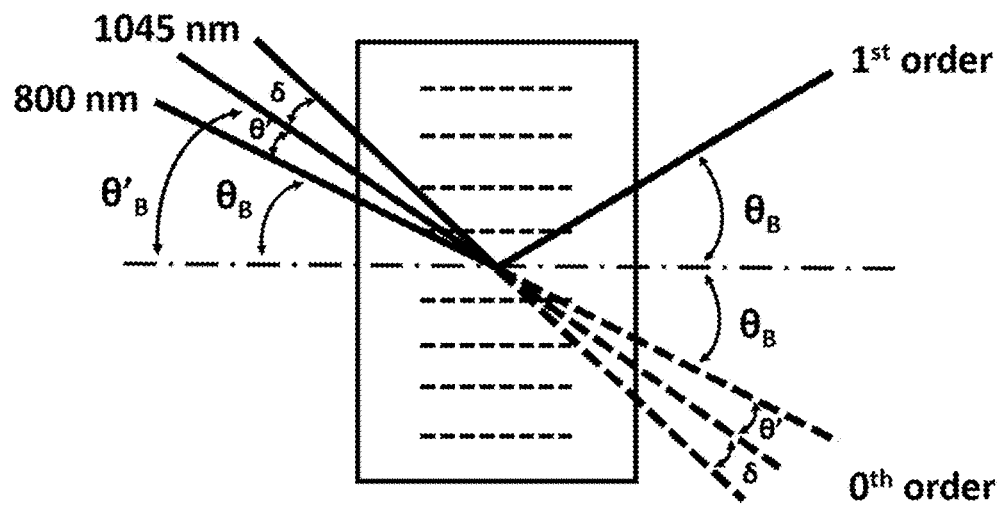
FIG. 2 is a schematic representation of spatial overlapping of the pump and Stokes beams at the $1^{st}$ order diffraction of the AOM depicted in FIG. 1.

The laser beam geometry at the AOM for spatially overlapping pump and Stokes beams along the $1^{st}$ order diffraction is illustrated in FIG. 2. In at least one embodiment the pump beam at 800 nm enters the AOM at the Bragg angle $\theta_B$. Both the $0^{th}$ and the $1^{st}$ diffraction orders of this wavelength have an angle of $\theta_B$ to the crystal surface normal. Assuming the Stokes beam at 1045 nm has a Bragg angle $\theta'_B = \theta_R + \theta'$, the incidence angle of this beam should be slightly detuned from $\theta'_B$ to generate the $1^{st}$ order diffraction in the same direction as the $1^{st}$ order pump beam. If $\delta$ is the angle between the incidence angle and the Bragg angle of the Stokes beam, it satisfies Equation 3:

$$\theta_{s,Stokes} = 2(\theta_B + \theta') = 2\theta_B + \theta' + \delta. \tag{3}$$

This gives $\delta = \theta'$, and indicates that when the pump and Stokes beams are collinear at the $1^{st}$ order of pump, the angle between the incidence and the Bragg angle of the Stokes beam equals the angle difference between the pump and Stokes Bragg angles. In one embodiment optical configuration, $\delta = 0.46°$. In embodiments using two mirrors in the Stokes-only beam path, the incidence angle of the Stokes beam at the AOM can be fine-tuned to satisfy this condition. In embodiments using this method, a 60% efficiency for the pump and 42% efficiency for the Stokes beam can be achieved using a 90% duty cycle. The loss of efficiency here is due to the suboptimal crystal anti-reflective coating and Bragg angle errors.

Pulse Picking for Sensitivity Improvement

Figure 3:
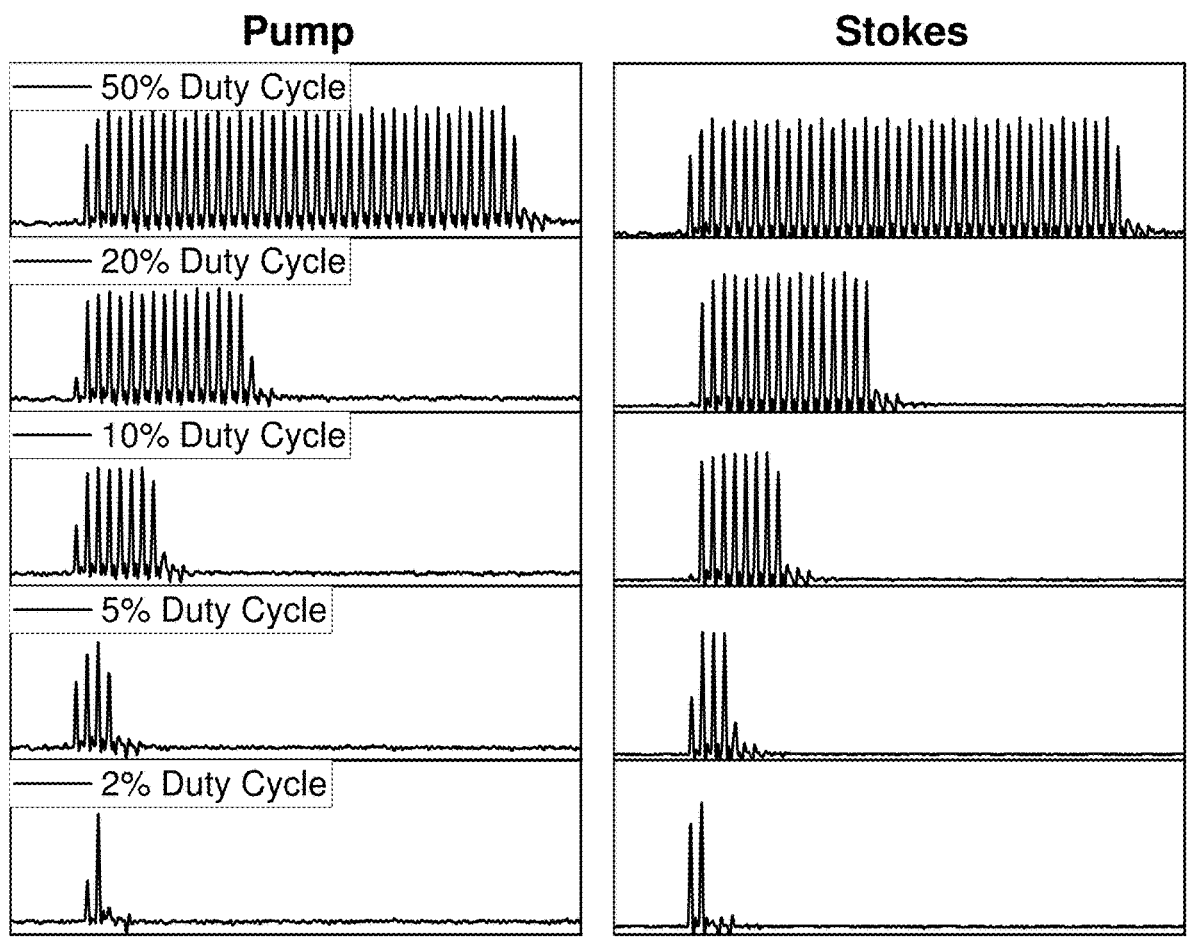
FIG. 3 is an example graphical representations of pump and Stokes pulse trains resulting from the AOM of FIG. 2 depicted in the $1^{st}$ order beam at 50%, 20%, 10%, 5%, and 2% duty cycles.
Figure 4A:
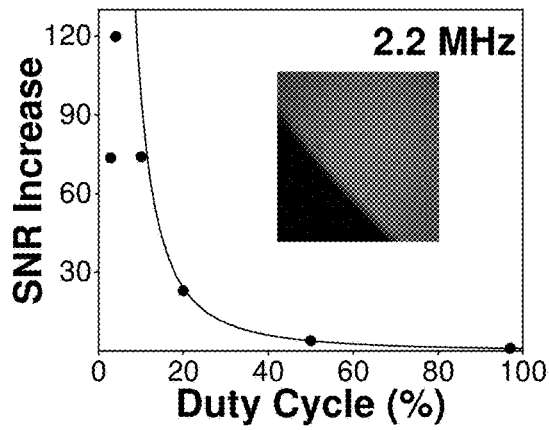
FIGS. 4A, 4B, 4C, and 4D are graphical representations depicting CARS signal-to-noise (SNR) increases versus duty cycle at 2.2, 1.1, 0.7, and 0.3 MHz modulation frequencies obtained from an example PPCARS microscope as represented by FIG. 1. The image inset depicts the edge of a sample of DMSO from which SNR values were derived. The dots are experimental data, curves are the theoretical function of $1/D^2$, and D is the duty cycle. The image inset shows a CARS image of dimethyl sulfoxide (DMSO) edge from which SNR values were derived.
Figure 4B:
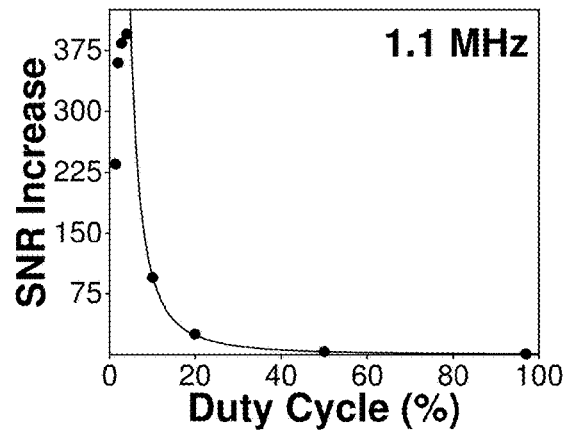
Figure 4C:
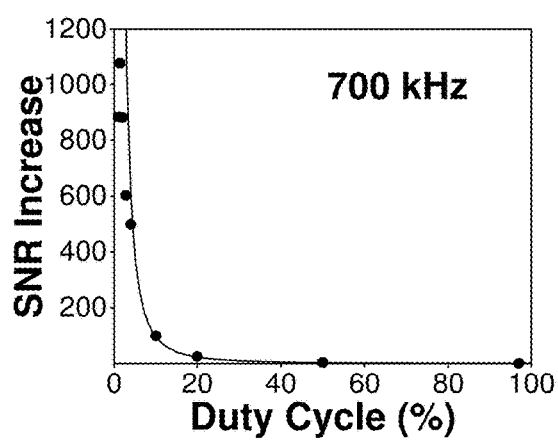
Figure 4D:
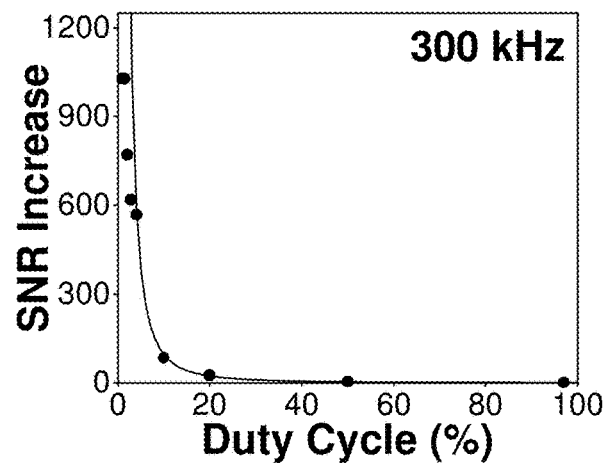

Laser pulses from both the pump and Stokes beams may be picked by the AOM at different duty cycle values. See, for example, FIG. 3. In some embodiments the rise time of the AOM is estimated to be approximately 23 ns for the Stokes and approximately 17 ns for the pump, which is slightly longer than the time interval between adjacent pulses from the laser and may be inferred from FIG. 3. At high duty cycles, the number of pulses picked by the AOM can be proportional to the duty cycle. For example, at 5% duty cycle, 4 major pulses can be picked for both pump and Stokes beams at 1.1 MHz modulation frequency. When the duty cycle is reduced to 2% or below, as few as one major pulse can be picked.

Reducing the laser duty cycle can enhance the sensitivity of nonlinear optical microscopy at the same input average power. For example, the intensity of the TPEF, SHG, and CARS signals can be expressed as the following in Equations 4 and 5:

$$I_{TPEF}, I_{SHG} \propto I_p^2, \tag{4}$$

$$I_{CARS} \propto |\chi^{(3)}|^2 I_p^2 I_s, \tag{5}$$

where $I_{CARS}$, $I_p$, and $I_s$ are, respectively, the intensities of the CARS, pump, and Stokes beams, and the SHG and TPEF signals are generated from the pump beam. $\chi^{(3)}$ is the third-order nonlinear optical susceptibility. The intensity of a laser pulse can be expressed as Equation 6:

$$I = \frac{E}{\tau A} = \frac{P}{f\tau A}. \tag{6}$$

Here, E, $\tau$, and A are pulse energy, pulse width, and laser focus area of the laser beam, while P and f are the laser average power and repetition rate, respectively. By modulating combined laser beams at a lower frequency and applying a duty cycle of D, we can arrive at Equations 7 and 8:

$$P_{TPEF}, (\text{or } P_{SHG}) = \tag{7}$$
$$fD\tau_{TPEF}A \cdot I_{TPEF} \propto fD\tau_{TPEF}A \cdot I_p^2 = fD\tau_{TPEF}A \cdot \left(\frac{P_p}{fD\tau_p A}\right)^2 \propto \frac{1}{D}$$

$$P_{CARS} = fD\tau_{CARS}A \cdot I_{CARS} \propto fD\tau_{CARS}A \cdot |\chi^{(3)}|^2 \left(\frac{P_p}{fD\tau_p A}\right)^2 \frac{P_s}{fD\tau_s A} = \tag{8}$$

$$|\chi^{(3)}|^2 \frac{P_p^2 P_s}{f^2 D^2 A^2} \frac{\tau_{CARS}}{\tau_p^2 \tau_s} \propto \frac{1}{D^2}$$

This indicates the pulse-picking CARS (PPCARS) average signal is reciprocal to the square of the duty cycle. Similarly, it can be seen that for the TPEF and SHG processes, the average signal is proportional to the reciprocal of D as expressed by Equation 9:

$$P_{TPEF}, P_{SHG} \propto \frac{1}{D}. \tag{9}$$

Chemical Imaging by a Pulse-Picking Nonlinear Optical Microscope

FIGS. 4A, 4B, 4C and 4D show a relationship between the sensitivity enhancement and duty cycle for FCARS signals at different modulation frequencies. In the embodiment used to produce FIG. 4A, a dimethyl sulfoxide (DMSO) $CH_3$ symmetric stretching peak at 2915 $cm^{-1}$ for the signal-to-noise ratio (SNR) analysis was used. A boundary of a DMSO drop sandwiched between two glass coverslips was imaged for SNR calculation. The SNR of the DMSO can be measured by dividing the average value of the DMSO signal by the standard deviation of the empty area. For each duty cycle measured in FIG. 4A, the SNR was divided by the SNR of the 97% duty cycle to calculate the sensitivity increase. A $1/D^2$ curve is plotted as a reference. It was determined that the experimental data matched the theoretical curve very well at high duty cycles, although at very low duty cycles the experimental data deviated from the theoretical curve in some embodiments. In some embodiments, the maximum sensitivity enhancement that was obtained was 1078 at 1.4% duty cycle, 700 kHz. One possible cause of the sensitivity drop at very low duty cycles might be related to the unlocked phase between the function generator modulation and the laser pulse train. Frequency drifts between the two can be less significant when the duty cycle is high since almost the same number of pulses can always be picked at any phase difference. However, when the duty cycle becomes low, especially below 4%, the phase drifts can significantly impact the number of pulses picked by the AOM.

FIGS. 5A and 5B depict correlations between modulation frequency and SNR increase at different duty cycles. These results show that at high duty cycles (>20%), the SNR increase is very similar at different modulation frequencies, while at low duty cycles (less than 20%), lower modulation frequency gives stronger SNR. The SNR decrease at 300 kHz may be due to the drift between modulation and acquisition of image pixels.

In embodiments utilizing fluorescent polystyrene beads, the fluorescence signal at 450 nm excited by 800 nm laser pulses (FIG. 6) was measured to evaluate the sensitivity enhancement of TPEF. For each duty cycle measured in FIGS. 4A, 4B, 4C and 4D, the signal-to-noise ratio (SNR) was divided by the SNR of the 97% duty cycle to calculate the sensitivity increase. A 1/D curve is plotted as a reference. The TPEF SNR increase shows a near 1/D relation at high duty cycles and starts to deviate from the theoretical curve at lower duty cycles.

In some embodiments it is possible to obtain a 16.3 sensitivity increase at a 2% duty cycle, 0.7 MHz. SHG signal improvement, which shows a similar dependence as the TPEF. An example of this sensitivity increase was measured using a mouse tail tendon specimen and 1045/522 nm excitation/detection as depicted in FIG. 7. In other embodiments it is possible to obtain a sensitivity increase of 14.5 at a 2% duty cycle, 1.1 MHz. Plots of TPEF/SHG SNR improvement versus duty cycle at other modulation frequencies can be plotted, and it can be shown that a sensitivity enhancement of approximately 20-fold can be achieved for both TPEF and SHG.

Figure 8A:
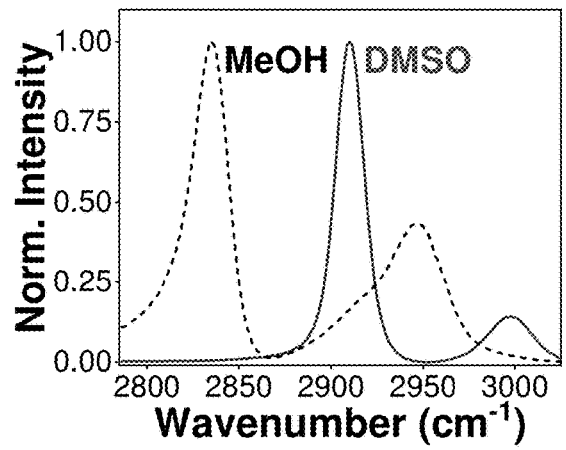
FIGS. 8A-8I are representations of information obtained from an example PPCARS microscope as represented by FIG. 1 with the power at the samples being 5.2 mW pump and 6.2 mW Stokes for the C—H imaging and 13.7 mW pump and 6.2 mW Stokes for the fingerprint imaging.
Figure 8B:
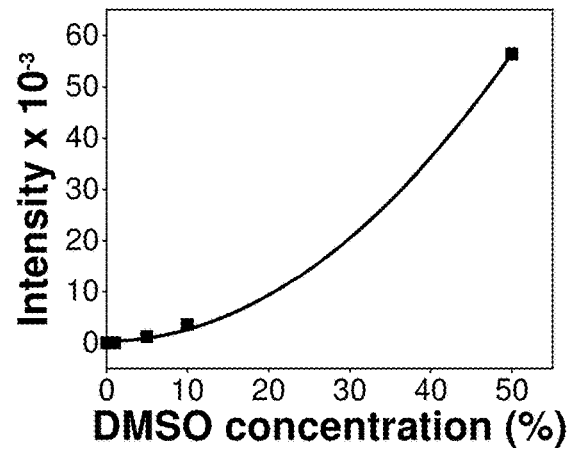
Figure 8C:
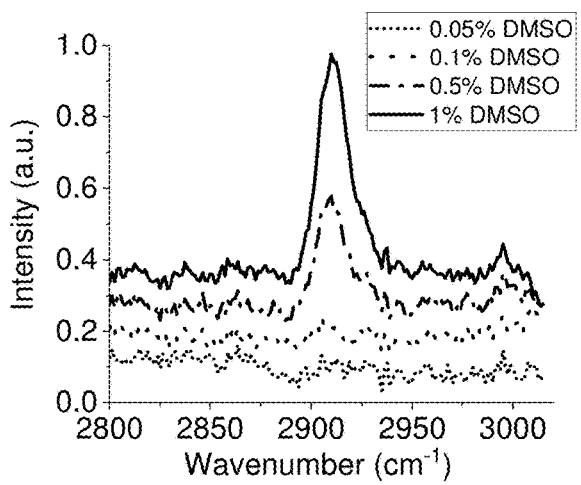
Figure 8D:
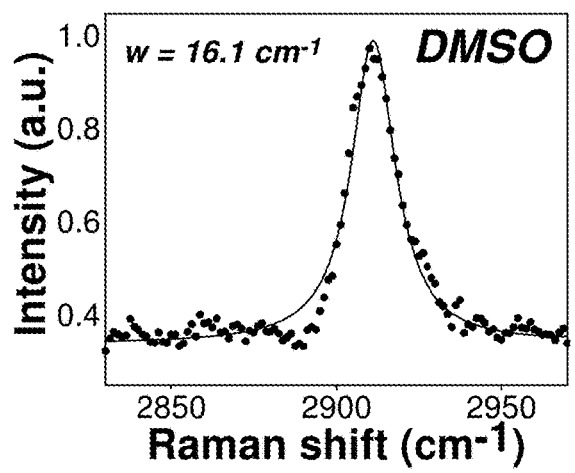

Measurements of the absolute sensitivity of microscopes according to embodiments of the present disclosure were performed using hyperspectral CARS imaging. A spectral phase retrieval method based on Kramers-Kronig relations was used to derive Raman spectra from chemical compounds using FCARS spectra. FIG. 8A shows CARS spectra of DMSO and methanol in the C—H stretching region. The sensitivity of a PPCARS system according to one embodiment of the present disclosure was measured using the 2915 $cm^{-1}$ peak of DMSO diluted in $D_2O$. The CARS signal intensity versus DMSO concentration is shown in FIG. 8B, from which a quadratic relationship, which agrees with equation 5, can be identified. Retrieved Raman spectra of DMSO below 1% concentration are shown in FIG. 8C. SNR calculations indicated that the lowest concentration detectable using 1.1 MHz modulation was 0.1%, corresponding to 14.2 mM DMSO. To detect such a concentration, embodiments with only a 5.2 mW pump (478 W peak power) and a 6.2 mW Stokes (1076 W peak power) can be used at the sample, and when these parameters are used with 1.1 MHz modulation, the lowest concentration detectable is between approximately 0.1% and 0.5% DMSO. In embodiments using a 0.7 MHz modulation with 2.0 mW pump (525 W peak power) and 3.7 mW Stokes (1835 W peak power) pulses, the DMSO symmetric stretching peak can be resolved for the 0.1% DMSO, corresponding to a concentration of 14 mM. By fitting the 2915 $cm^{-1}$ DMSO peak using a Lorentzian function, as shown in FIG. 8D, the spectral resolution of the embodiment system was measured at 16.1 $cm^{-1}$ in the C—H region.

Figure 8E:
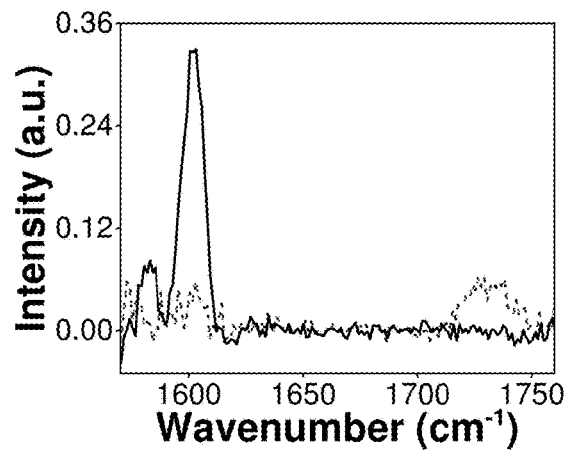
Figure 8F:
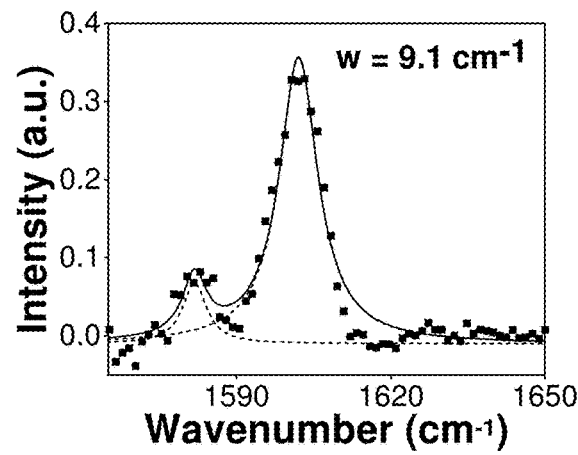

FIG. 8E plots retrieved Raman spectra of polystyrene (PS) and polymethyl methacrylate (PMMA) in the 1570-1750 $cm^{-1}$ Raman fingerprint region acquired using 1 μm PMMA and PS mixed particles. The PS peaks at 1583 (C=C stretching) and 1602 cm$^{-1}$ (ring-skeletal stretching) can be resolved, while a PMMA peak at 1736 cm$^{-1}$ is also detected. Using the strong peak at 1602 cm$^{-1}$, a 9.1 cm$^{-1}$ CARS spectral resolution was measured in this region when using a microscope according to one embodiment of the present disclosure, as shown in FIG. 8F.

Figure 8G:
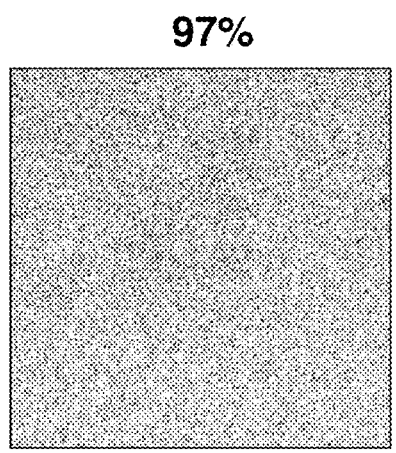
Figure 8H:
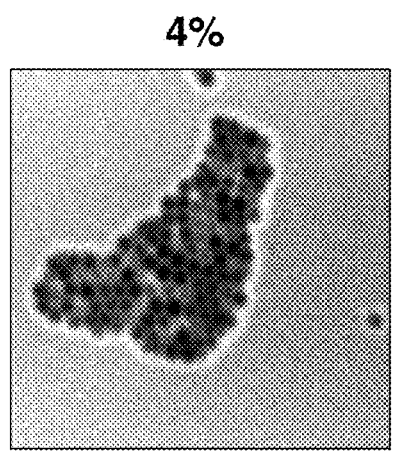
Figure 8I:
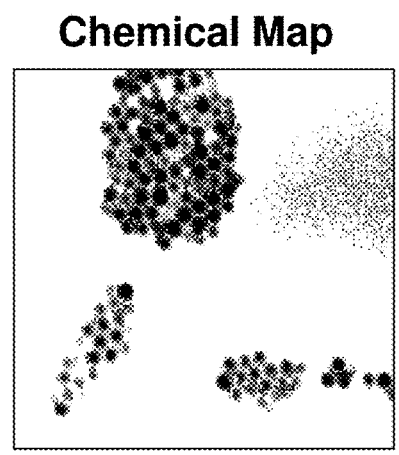
Figures 9A, 9B, 9C:
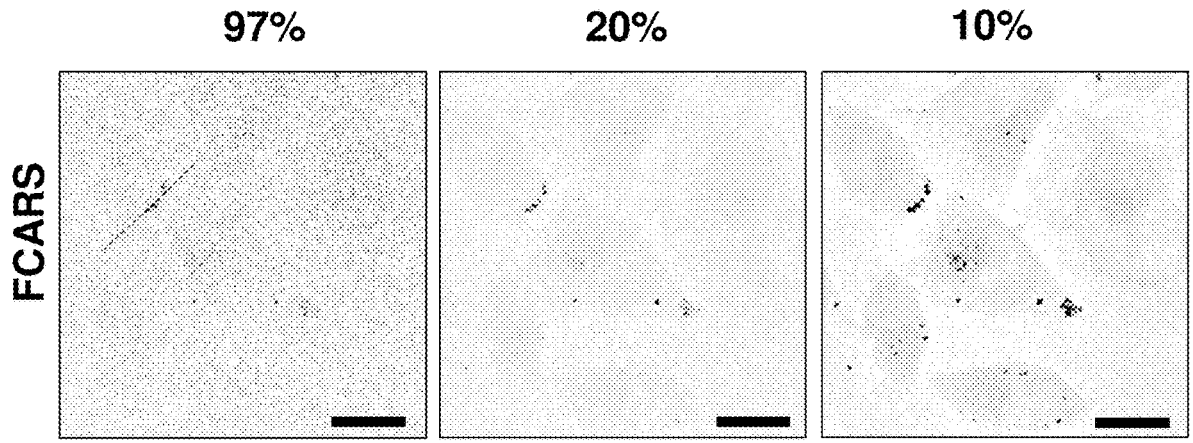
Figures 9D, 9E:
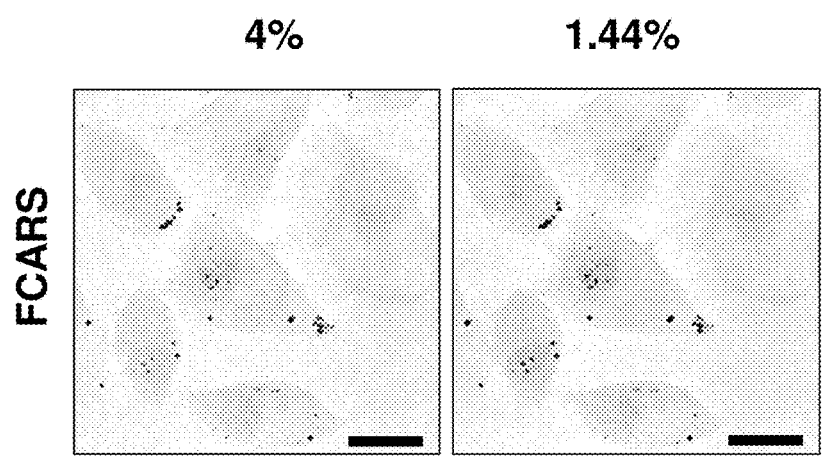
Figures 10A, 10B, 10C:
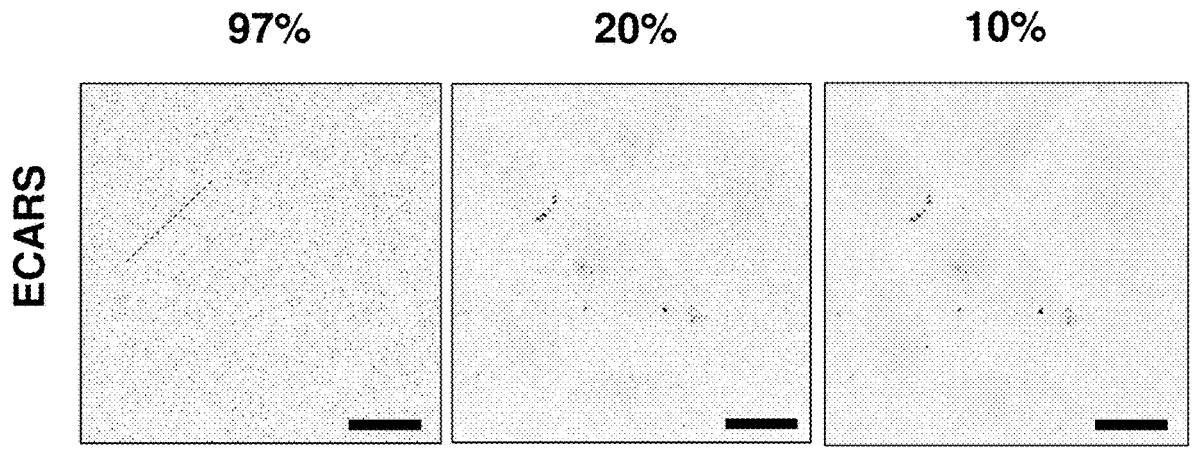
Figures 10D, 10E:
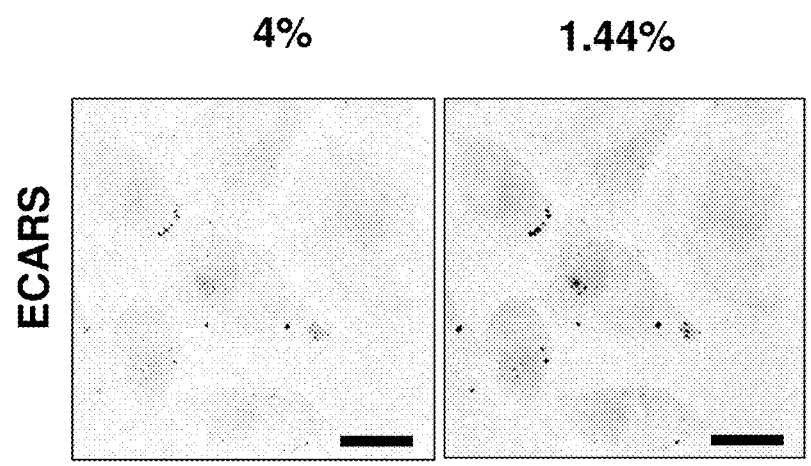

FIGS. 8G and 8H compare CARS images of mixed PMMA and PS beads at approximately 1602 cm$^{-1}$ using 97% and 4% duty cycles. A clear SNR and contrast improvement can be seen at the reduced duty cycle. By spectral phasor analysis of hyperspectral CARS images in the fingerprint region, embodiments of the present disclosure were able to separate PMMA and PS microparticles, as shown in FIG. 8I. For fingerprint imaging, 13.7 mW pump and 6.2 mW Stokes beams at the sample with a 10 µs pixel dwell time delivered good results.

Cell Imaging by a Pulse-Picking Nonlinear Optical Microscope

Figure 11A:
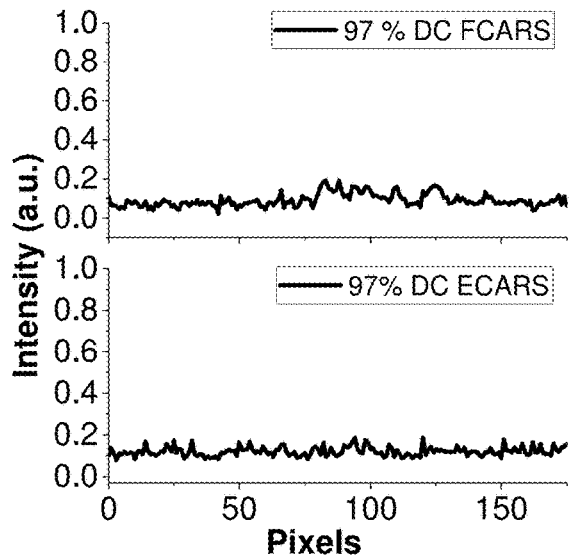
Figure 11B:
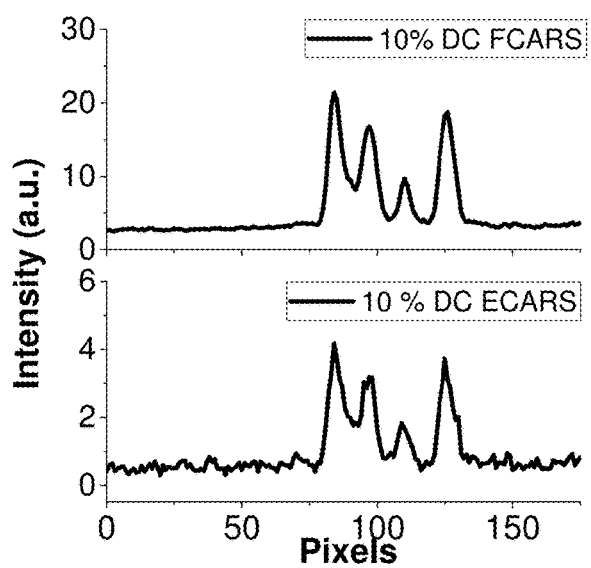
Figure 11C:
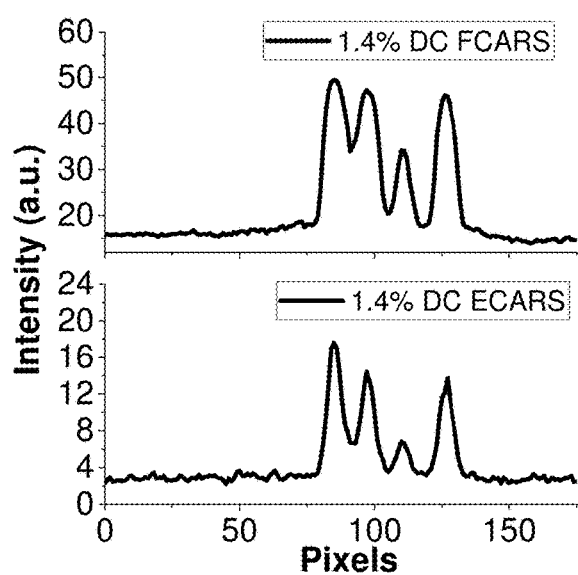
Figures 12A, 12B, 12C:
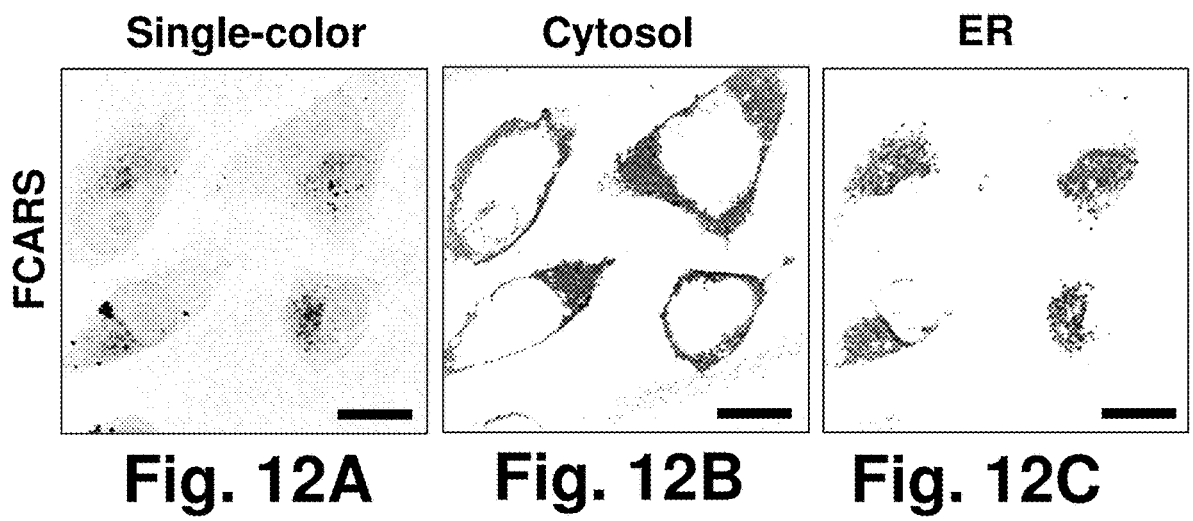
FIGS. 12A, 12B, 12C, 12D and 12E include single-color CARS (FIG. 12A) and spectral unmixing images (Cytosol (FIG. 12B), endoplasmic reticulum (ER, FIG. 12C)), nuclei (FIG. 12D) and lipid droplets (LD, FIG. 12E)) for Mia PaCa-2 cells obtained from an example PPCARS microscope as represented by FIG. 1.
Figures 12D, 12E:
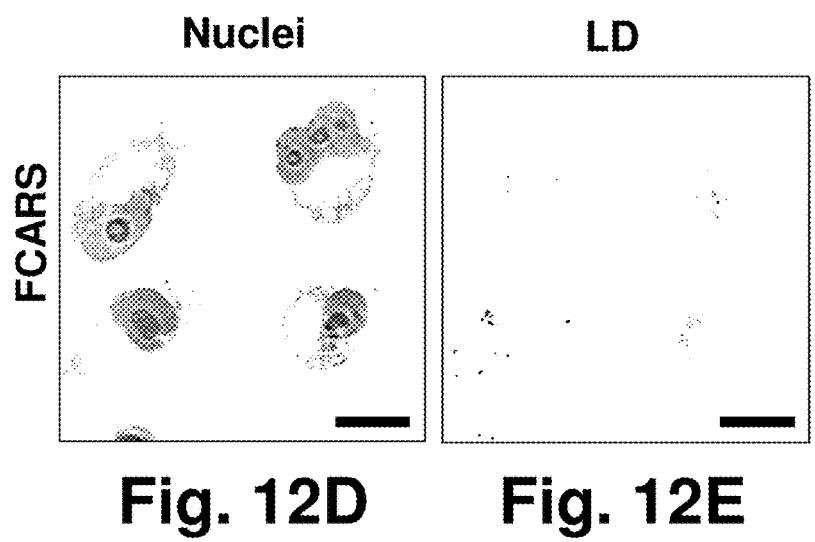

PPCARS according to embodiments of the present disclosure can be used for cell imaging. FIGS. 9A-10E compare two types of pulse-picking CARS for cell imaging, namely single-color FCARS (FIGS. 9A-9E) and ECARS (FIGS. 10A-10E) images from Mia PaCa-2 cells at different duty cycles: 97% duty cycle (FIGS. 9A and 10A), 10% duty cycle (FIGS. 9C and 10C), and 1.4% duty cycle (FIGS. 9E and 10E) duty cycles. For these images a 700 kHz modulation frequency was used and a continuous increase in signal and sensitivity for both FCARS and ECARS was observed as the duty cycle decreased from 97% to 1.4%. For a comparison of the sensitivity improvement, the intensity profiles along the lines in FIGS. 9A and 10A were plotted along the lines in FIGS. 11A, 11B, and 11C, which show an approximately 250×(250 times) signal improvement at the 1.4% duty cycle. However, it is possible that the sensitivity enhancement for small lipid droplets in the cells may be less than the pure samples shown in FIGS. 3-7, which may be due to a higher ratio of nonresonant contribution at laser focus. Power at the sample for these images was 10.8 mW for the pump and 5.0 mW for the Stokes, and cell imaging results using low duty cycles at 1.1 MHz modulation frequency were very good. Live-cell imaging of lipid droplets and mitochondria can also be performed using CARS and TPEF signals from a mitochondria marker.

Figure 13:
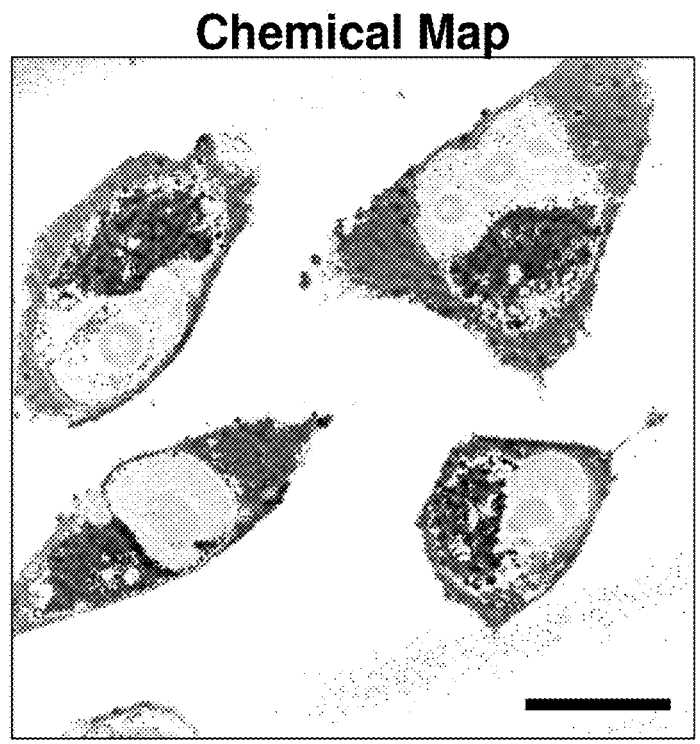
Figure 14:
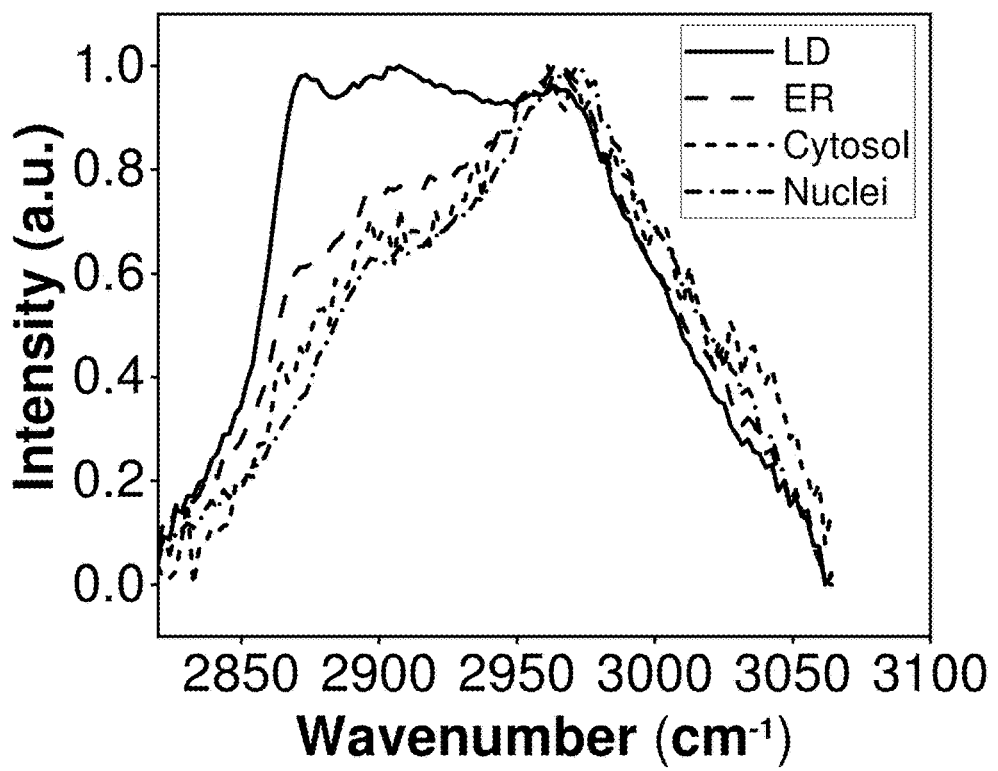
Figure 19A:
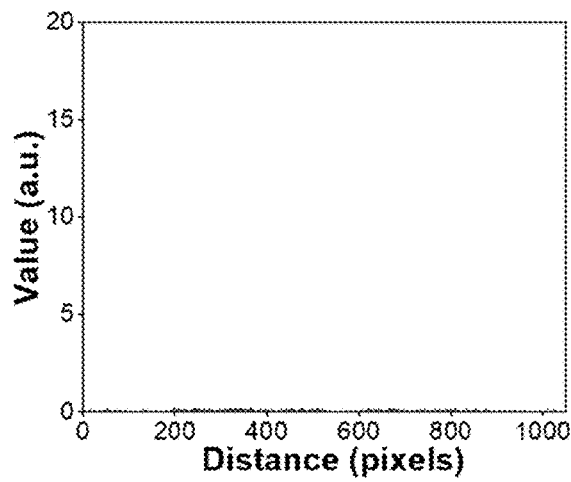
FIGS. 19A, 19B, 19C, and 19D are line profile plots along the dashed line depicted in FIGS. 15B, 16B, 17B and 18B. The 97% line profiles for FCARS and ECARS are multiplied by 10.
Figure 19B:
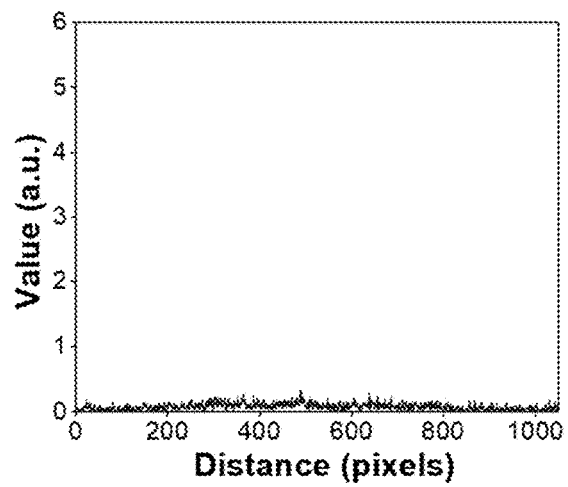
Figure 19C:
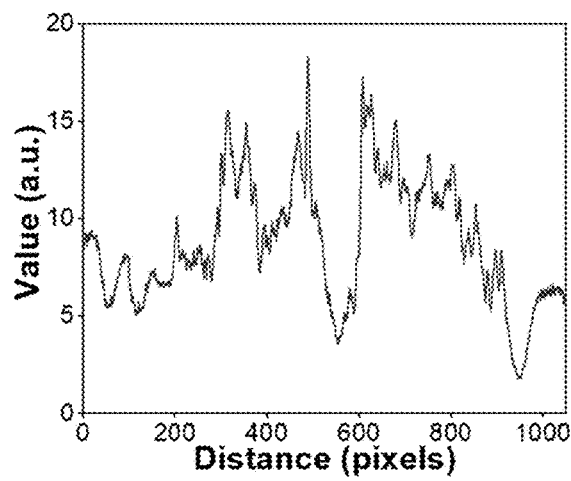
Figure 19D:
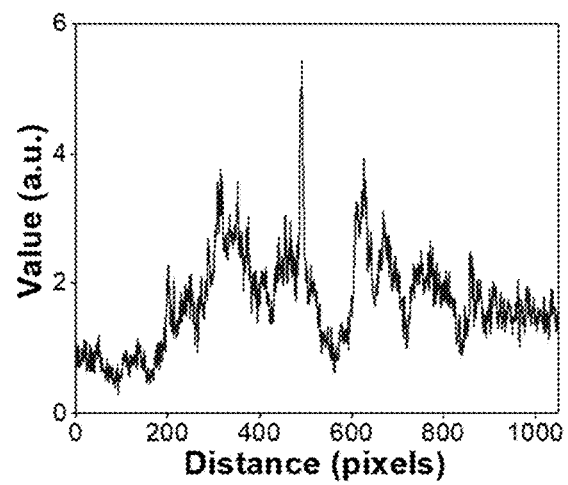
Figure 20A:
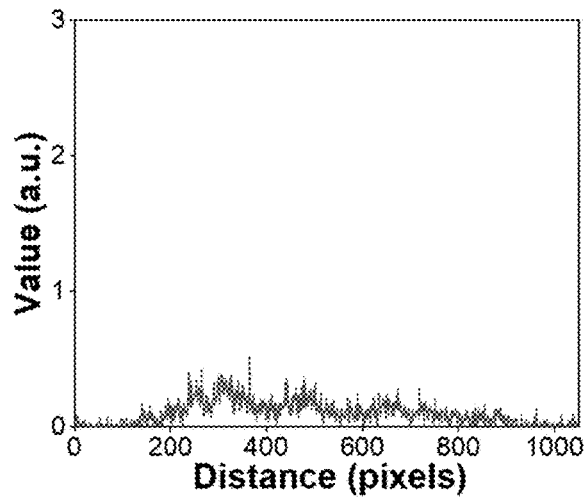
FIGS. 20A, 20B, 20C, and 20D are line profile plots along the dashed line depicted in FIGS. 15B, 16B, 17B and 18B. The 97% line profiles for FCARS and ECARS are multiplied by 10.
Figure 20B:
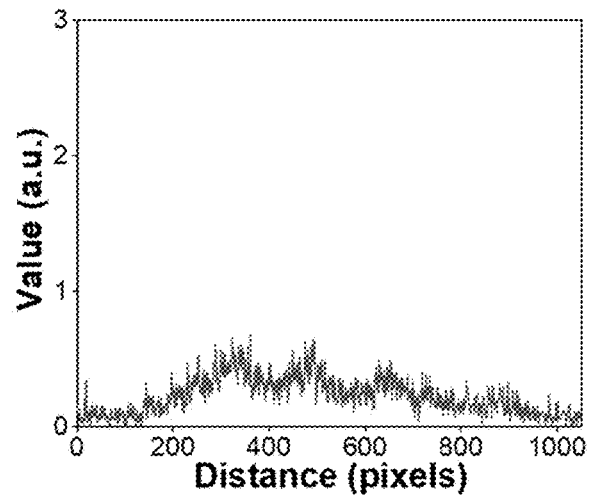
Figure 20C:
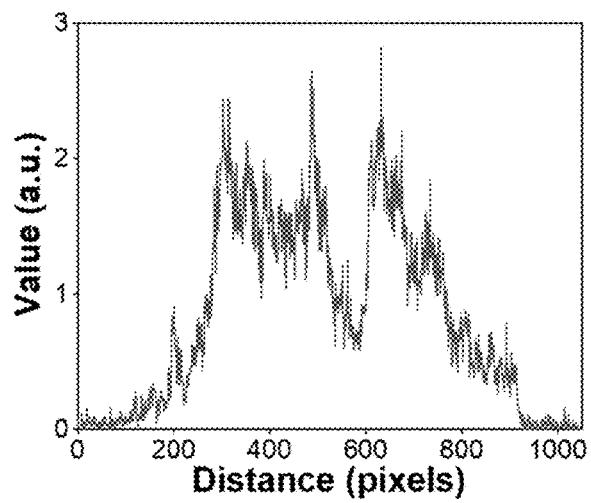
Figure 20D:
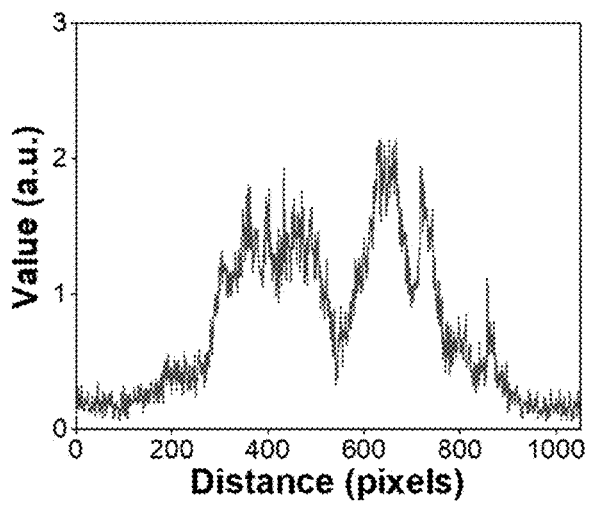

Hyperspectral CARS images of cells can be performed using 2.0 mW pump and 3.7 mW Stokes excitation power at 10 µs pixel dwell time. By spectral focusing and spectral phasor unmixing, major cellular compositions including cytosol, endoplasmic reticulum, nuclei, and lipid droplets in cells can be separated using both FCARS (FIGS. 12A, 12B, 12C, 12D and 12E) and ECARS images. The composited chemical map of cells and retrieved Raman spectra of four major components using FCARS are shown in FIGS. 13 and 14, respectively. The separation capability of embodiments of the present disclosure using hyperspectral CARS microscopy is comparable to spectral-focusing-based hyperspectral SRS. 3D imaging of a Mia PaCa-2 cell can also be performed using embodiments of the present disclosure, demonstrating the 3D chemical imaging capability of the PPCARS microscope of the present disclosure.

Tissue Imaging by a Pulse-Picking Nonlinear Optical Microscope

Evaluation of sensitivity enhancements using a pulse picking method (for example, those using multimodal microscopes) for tissue imaging according to embodiments of the present disclosure can be carried out using FCARS, ECARS, TPEF at 450 nm, and TPEF at 570 nm images of mouse liver tissue at 97% and 4% duty cycles under 1.1 MHz modulation (FIGS. 15A-18B) and comparing these methods to one another. CARS excitation wavelengths can be tuned to the CH$_2$ stretching at 2855 cm$^{-1}$. Signals in the TPEF 450 nm channel can have significant contributions from the autofluorescence from nicotinamide adenine dinucleotide (NADH) while signals in the TPEF 570 nm channel can have significant contributions from the autofluorescence from flavin adenine dinucleotide (FAD).

Figure 21A:
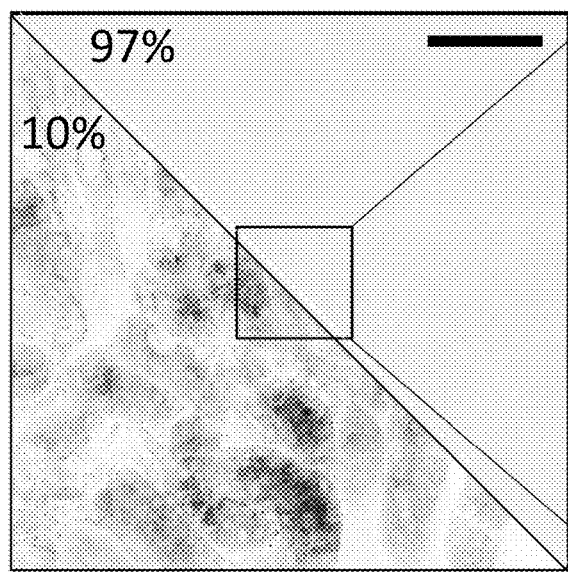
FIGS. 21A and 21B are side-by-side comparisons of 10% and 97% duty cycles for ECARS imaging of a mouse kidney sample with an enlarged depiction of the boxed region of FIG. 21A represented in FIG. 21B.
Figure 21B:
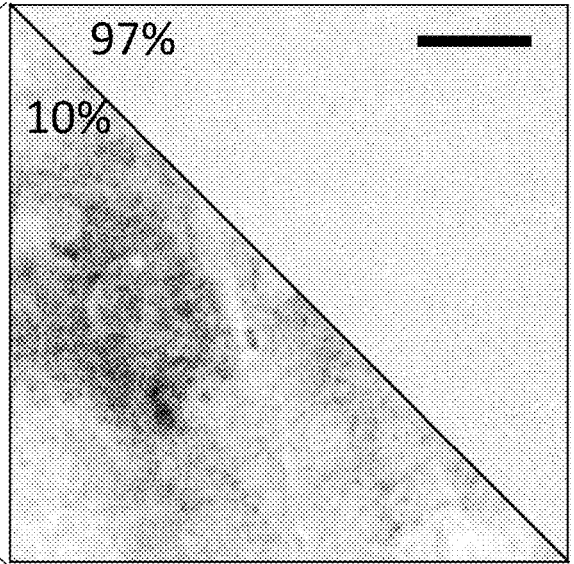
Figure 22A:
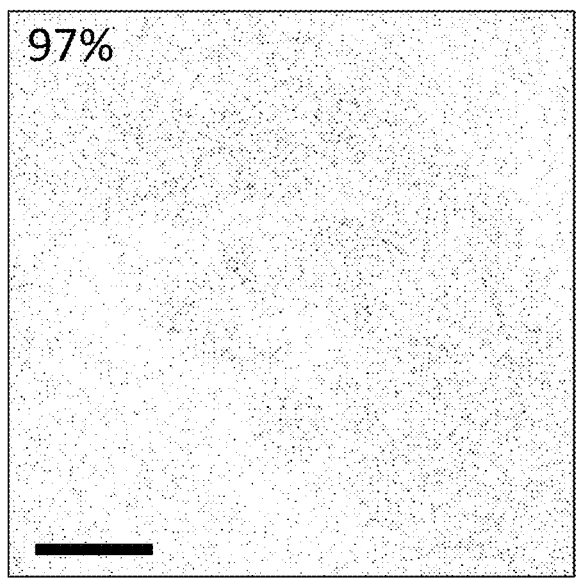
Figure 22B:
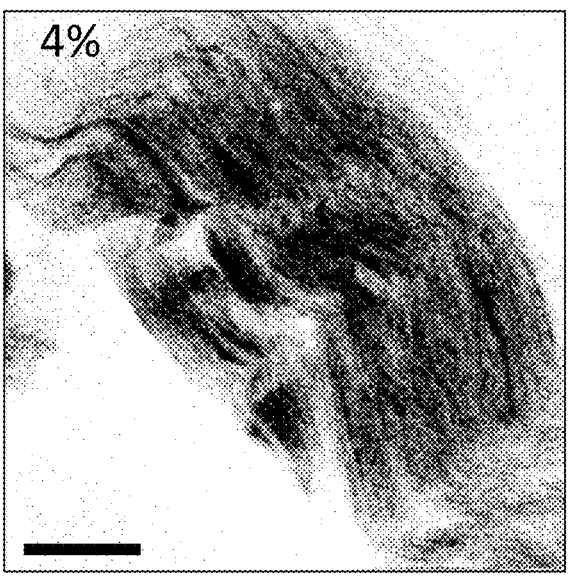
Figure 23A:
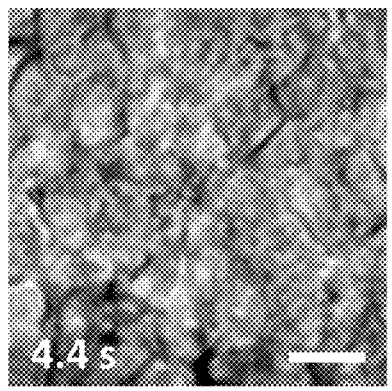
Figure 23B:
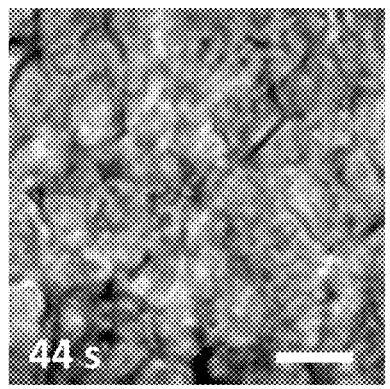
Figure 23C:
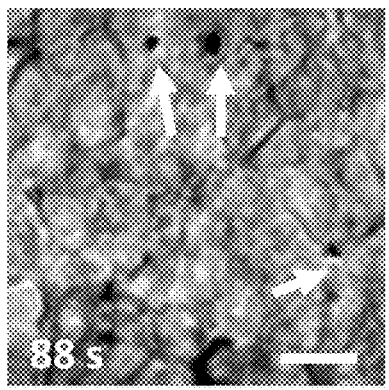
Figure 23D:
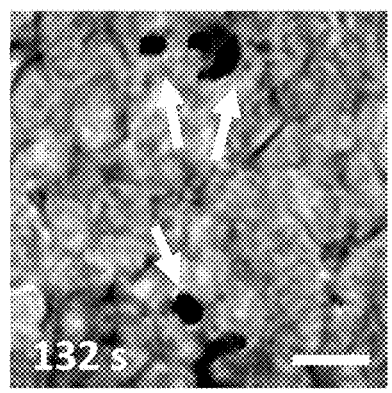
Figure 23E:
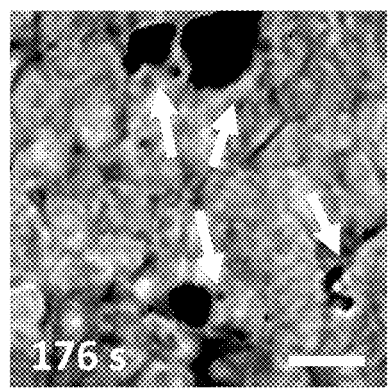
Figure 24A:
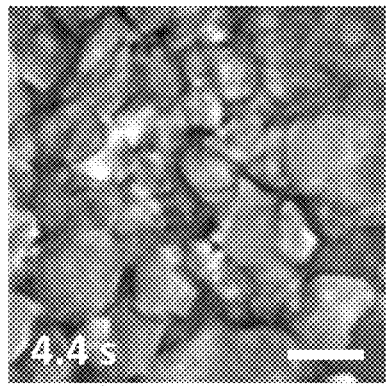
FIGS. 24A, 24B, 24C, 24D and 24E depict time-lapse imaging of a mouse spleen tissue sample at a 5% duty cycle of picosecond pulses with a pump of 7.5 mW (551 W) and a Stokes of 5 mW (694 W). The scale bar is 10 μm.
Figure 24B:
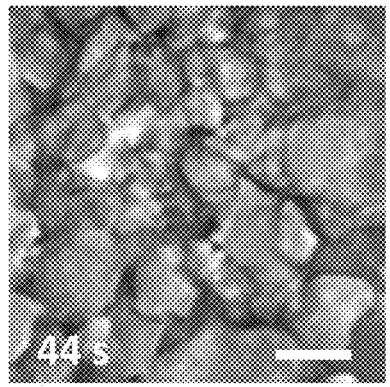
Figure 24C:
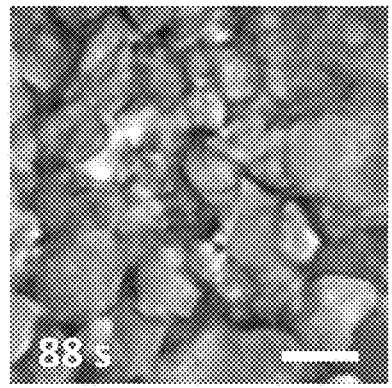
Figure 24D:
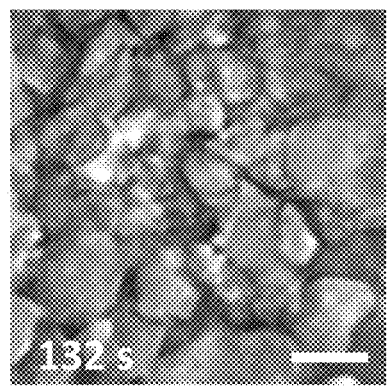
Figure 24E:
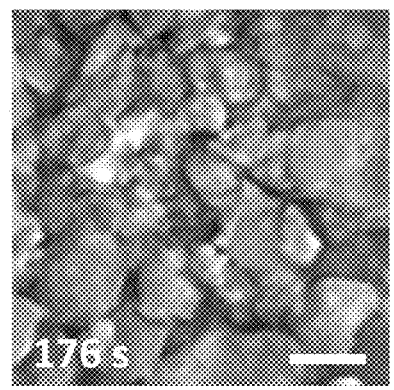
Figure 25A:
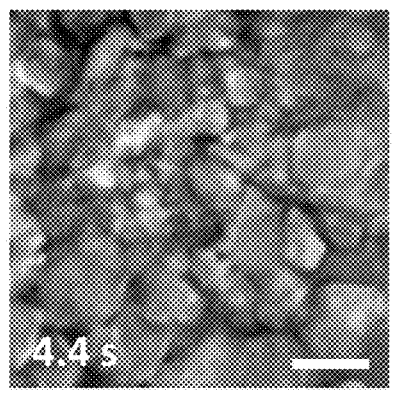
Figure 25B:
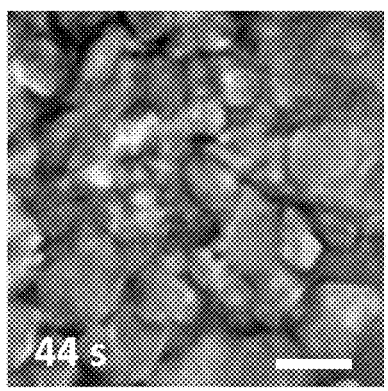
Figure 25C:
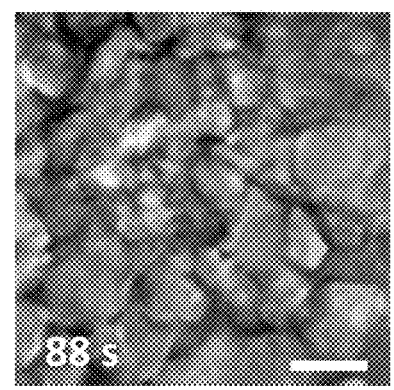
Figure 25D:
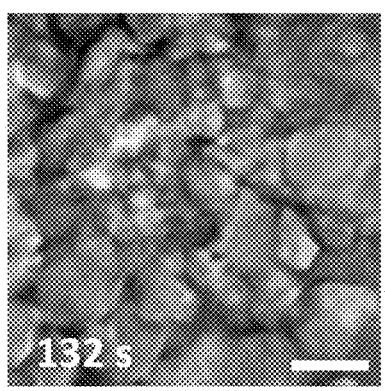
Figure 25E:
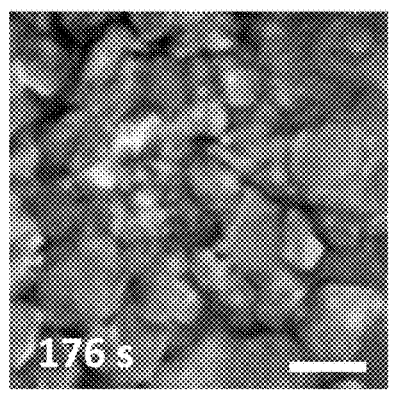

Depicted in FIGS. 15A-18B are comparisons of the contrast enhancement brought about by utilizing these FCARS, ECARS, and TPEF techniques. In each of FIGS. 15A, 16A, 17A and 18A is a depiction of two separate duty cycle images positioned side-by-side into a single image and separated along the diagonal extending from the upper left corner of the image to the lower right corner of the image. In each of FIGS. 15B, 16B, 17B and 18B is an expanded view of the portion indicated by the square in each of FIGS. 15A, 16A, 17A and 18A. FIGS. 19A-20D depict intensity profiles taken along the dashed lines in FIGS. 15A-18B. These results show strong SNR enhancement for all modalities at 4% duty cycle. ECARS mouse kidney tissue images at 97% and 10% duty cycles are displayed in FIGS. 21A and 21B, demonstrating sensitivity increase at a moderate duty cycle. Sensitivity enhancements of SHG imaging using mouse tail tendon are depicted in FIGS. 22A and 22B. Images from other tissue samples and at other modulation frequency/duty cycles were also used, and the results demonstrated the usefulness of pulse picking technology for the chemical analysis of intact biopsy samples for diagnostics.

Photodamage of Tissue Samples at Different Average and Peak Power Levels

Figure 26A:
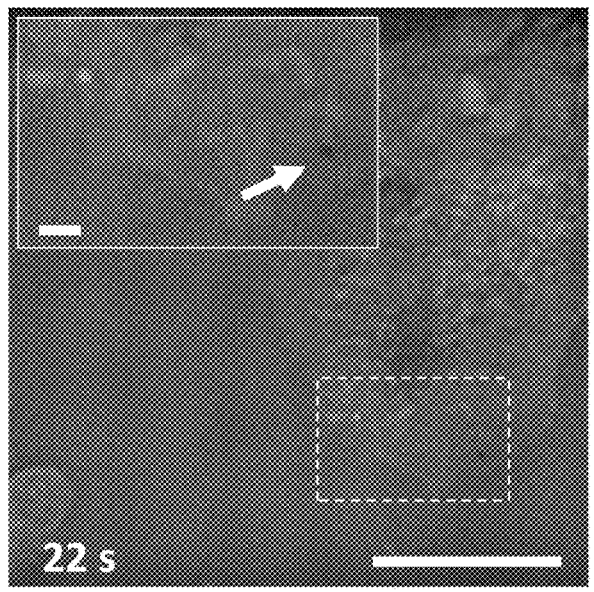
FIGS. 26A, 26B, and 26C depict pulse picking of femtosecond laser pulses with a pixel dwell time of 20 μs. The arrows indicate multiphoton-absorption-induced photodamage. The scale bar is 1 μm.

Pulse-picking embodiments of the present disclosure can significantly reduce thermally induced photodamage via single-photon absorption; however, there is still a potential risk of increasing multiphoton-absorption-induced phototoxicity. To evaluate and compare phototoxicity in different conditions, embodiments utilizing CARS were used maintaining the same sensitivity and image quality based on the curves shown in FIGS. 4A, 4B, 4C and 4D while changing duty cycles, which resulted in different average and peak power combinations. FIGS. 23A-25E show time-lapse CARS images of a mouse spleen section produced by decreasing the average power and increasing the peak power with a pixel dwell time of 20 µs. When using high average power and low peak power on the sample (see, FIGS. 23A-23E), obvious photodamage was observed starting from 88 s of laser scanning. The damaged area also continued to enlarge after longer laser exposure. However, at lower average power and higher peak power (see, FIGS. 24A-24E and 25A-25E), no detectable photodamage was observed. These results indicate that embodiments of the present disclosure with laser pulses of approximately 12.5 mW combined average power and approximately 3600 W combined peak power are safe for mouse spleen imaging. Still further, embodiments with duty cycles reduced to less than 5% of 80 MHz ps pulse trains produced results with high sensitivity and low phototoxicity. Additional embodiments bypass the chirping rods and apply the same method for picking fs laser pulses. As shown in FIG. 26A, photodamage was detected at 44 s with embodiments having peak power of over 10,000 W in the Stokes beam despite the average power on the sample being very low.

Figure 26B:
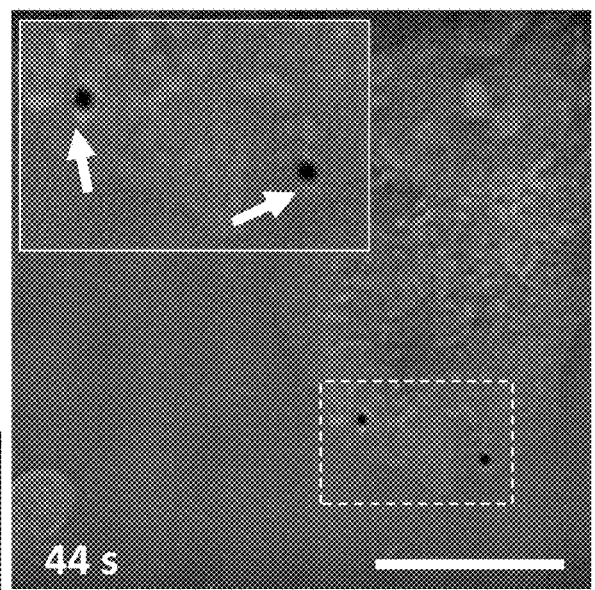
Figure 26C:
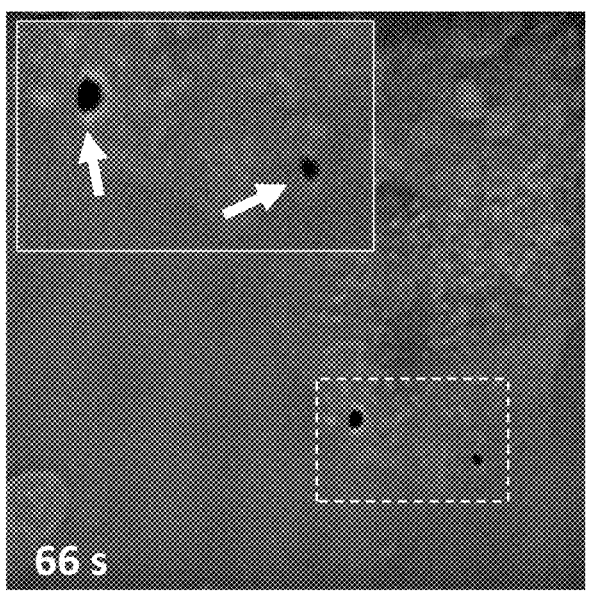

FIGS. 26A-26C depict an embodiment using a mixed MIA PaCa2 cell as the target sample. Here it was expected that the laser pulses would induce more photodamage with a mouse spleen as the target than with the cultured cells as the target. Nevertheless, the results demonstrated that both the high average and high peak power of the laser pulses can induce photodamage to biological samples. For embodiments utilizing CARS imaging, combined average power of less than 12.5 mW and a combined pulse peak power of less than 3600 W on the sample appeared to be safe for a mouse spleen target at 20 μs pixel dwell time. These parameters were also satisfactory for embodiments utilizing TPEF, and SHG imaging. The pulse picking methods according to embodiments of the present disclosure enable optimal integration of hyperspectral CARS, TPEF and SHG in a single imaging platform that can use chirped femtosecond (chirped to picosecond) laser pulses. Different tissue samples can have different power safe-range and can be evaluated similarly using the pulse picking methods disclosed herein.

Lipid Droplet Dynamics for Quantification of Laser Phototoxicity

Figure 27:
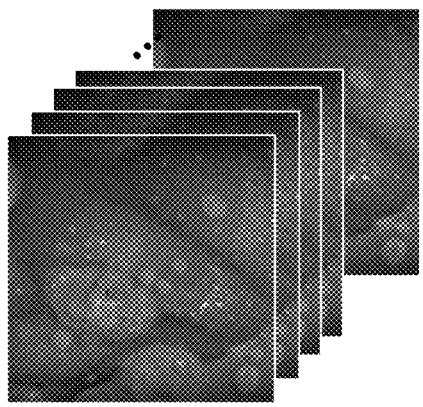
FIG. 27 depicts an illustration of the workflow for CARS image stack acquisition, Lipid droplet (LD) trajectory tracing and quantitative analysis of the LD dynamics. Quantifying LD intercellular dynamics and evaluating phototoxicity were performed at different average (4-60 mW) and peak power (44-1984 W) levels. The pixel dwell time was 10 μs.
Figure 27:
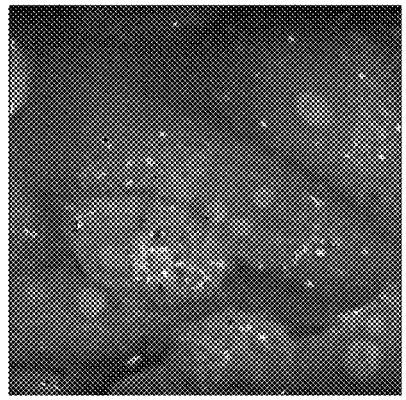
Figure 27:
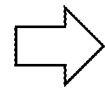

Measuring laser phototoxicity and light-induced perturbation to cells is a challenging yet essential task for label-free imaging of live cells. Conventional techniques rely on monitoring cell shrinkage or membrane blebbing to identify severe photo-damage to cells. Cells showing these obvious structural and dynamic features have been strongly perturbed and in the late stage of photo-induced apoptosis. Here, intercellular dynamics are used to quantify photo-perturbation to live cells. Intercellular organelle dynamics are powered by ATP, and therefore are more sensitive to probe and quantify perturbations to cells. It was shown that lipid droplet (LD) dynamics can be applied to quantify cell responses to temperature change and drug treatment. LD dynamics are applied to evaluate photo-perturbation by laser pulses at different average and peak power ranges achieved by the pulse picking method described in this disclosure. FIG. 27 illustrates the workflow of performing LD dynamics analysis to quantify photo-perturbation of live cells. FIGS. 28A-28D compare LD maximum displacement at different average and peak power levels. These results suggested that pulse picking allows to achieve low average power and high peak power range that gives minimum LD maximum displacement decrease, which indicates minimum phototoxicity to live cells.

Figure 28A:
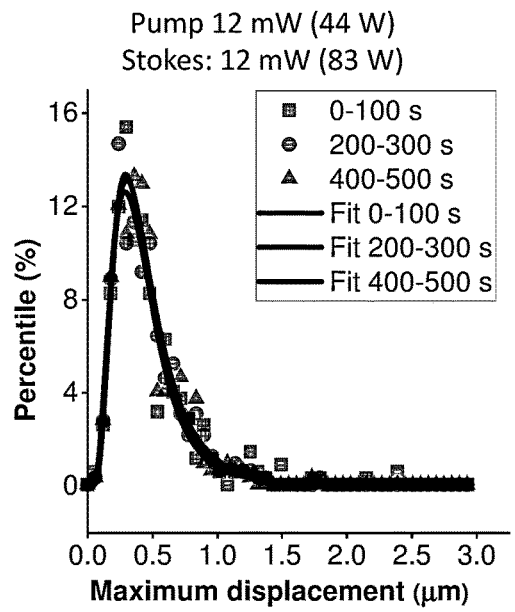
FIGS. 28A, 28B, 28C, and 28D depict histograms of LD maximum displacement (in μm) in HeLa cells using the methodology depicted in FIG. 27 with low average power and low peak power pulses (see, FIG. 28A), low average power and high peak power pulses (see, FIG. 28B), and high average power and low peak power pulses (see, FIG. 28C). The dots represent the experimental data from the different time windows and the curves are Lognormal fitting results.
Figure 28B:
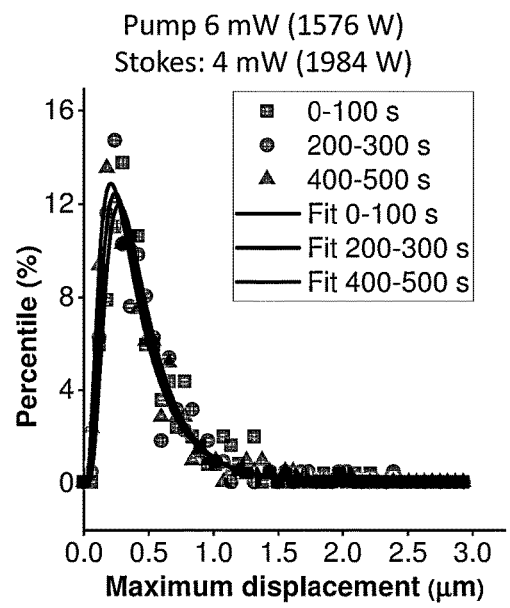
Figure 28C:
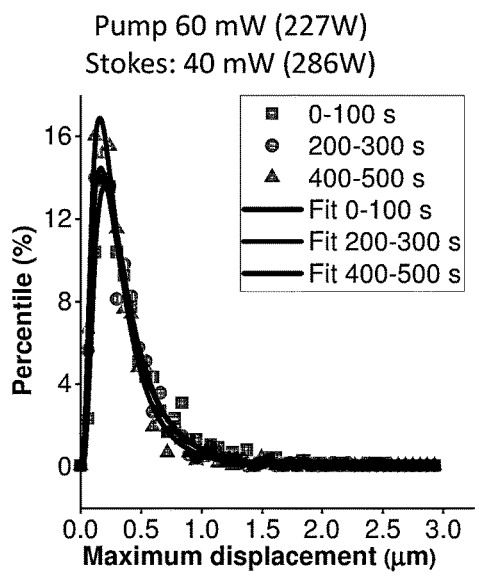
Figure 28D:
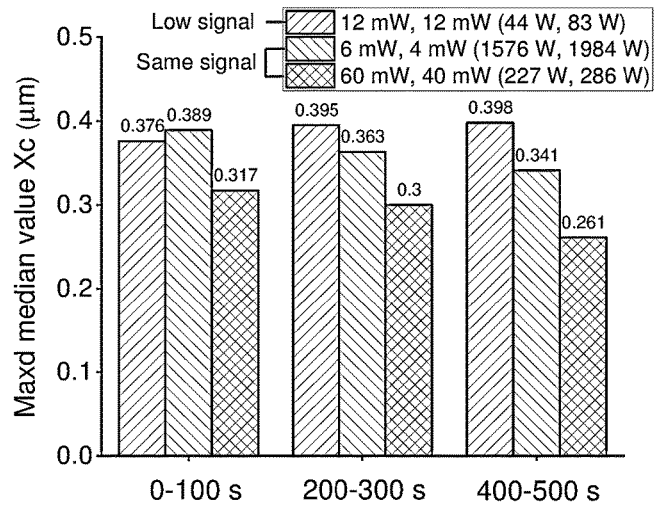

FIG. 27 is an illustration of the workflow used for data acquisition and analysis. The maximum displacement of LDs over the image acquisition time was used to evaluate photo-perturbation to live HeLa cells. Multiple (for example, fifty) images were collected at 10 μs per pixel (2 s per frame). The trajectory tracking of LDs was performed using a particle tracker, for example, an ImageJ plugin, and a lab-written MATLAB code was used to perform quantitative and statistical data analysis. Histograms of LD maximum displacement at 3 time windows (0-100 s, 200-300 s, and 400-500 s) are plotted and compared in FIGS. 28A, 28B and 28C for different power ranges: Pump 12 mW (44 W) and Stokes 12 mW (83 W); Pump 6 mW (1576 W) and Stokes 4 mW (1984 W); and Pump 60 mW (227 W) and Stokes 40 mW (286 W) respectively. A low average power (less than 24 mW total) and peak power (less than 130 W total) condition was measured (FIG. 28A), which was shown to be safe for live-cell imaging and showed almost no changes in LD dynamics over 500 s laser exposure. Next, the image contrast was significantly increased using pulse picking at the low average power (less than 10 mW total) and very high peak power (approaching 3600 W total) condition (1.4% pulse picking). The LD dynamics analysis results are shown in FIG. 28B. The results were very similar histogram profiles as depicted FIG. 28A. Maintaining the same image contrast, the high average power (100 mW total) and low peak power (about 500 W total) condition (FIG. 28C) was also compared to FIG. 28A, which showed a significant decrease in the maximum displacement values from 1-100 s. This dynamic signature change was correlated with apoptosis and strong cellular perturbations. Longer exposure time continues to decrease the maximum displacement values, as shown in FIG. 28C. To quantitatively compare the shifts of maximum displacement histograms, the experimental data were fitted with lognormal functions and the median values of the maximum displacement ($x_c$) were obtained. A quantitative comparison of the $x_c$ values in FIG. 28D demonstrates that at the same imaging contrast the high peak power condition used in the above-described experiment gives less of a decrease in $x_c$ compared to the high average condition, indicating less phototoxicity to live cells as compared to conventional imaging.

From these LD dynamic analyses, a total average power of less than 24 mW and a total peak power of less than 3600 W are safe conditions for live-cell imaging when using embodiments of the present disclosure. To achieve the same imaging quality, existing methods require a total average power of 100 mW and a total peak power of 500 W, which results in stronger phototoxicity. While the safe and optimal power ranges for different cells might be different and are also relevant to the pixel dwell time, scanning range, and the size of the focus, the pulse picking method of the present disclosure provide better imaging results and less phototoxicity than existing methods.

Example Embodiments and Optimization

Embodiments of the present disclosure provide a pulse picking technology to, for example, increase the sensitivity of multiple nonlinear optical imaging modalities including but not limited to CARS, TPEF, and SHG. Embodiments use function-generator-controlled AOM and apply at least one of the excitation beams at a Bragg angle error condition and collinearly combined both pump and Stokes beams at the 1$^{st}$ order of AOM. In embodiments where the duty cycle of the laser beams is reduced, improvements in the SNR and/or CARS imaging occurred up to 1078 times for pure samples. Some embodiment methods offer about 20 times sensitivity enhancement for TPEF and/or SHG. With 10 μs pixel dwell time, hyperspectral PPCARS according to embodiments of the present disclosure can detect 7 mM DMSO in deuterated oxide with less than 6 mW total excitation power on the sample. The low excitation power and short pixel dwell time used in some embodiments significantly reduce, and possibly minimize, the phototoxicity of lasers for nonlinear optical imaging.

Above the 10% duty cycle, the sensitivity enhancements for all nonlinear optical processes according to embodiments of the present disclosure appear to match theoretical predictions. Below 10%, deviations can increase between the experimental results and the theoretical curve. The optimal duty cycle appears to vary at different modulation frequencies, while the optimal modulation frequency appears to be dependent on the pixel dwell time. What appeared to be optimal duty cycle values tended to decrease at lower modulation frequencies.

The decrease in sensitivity improvement for CARS at very low duty cycles may be due to the pulse picking variations and drifts caused by an unlocked phase between the laser repetition frequency and the modulation frequency, and possibly rise time differences between pump and Stokes pulses. These variations exist at the rise and fall time of each cycle, and are not significant for high duty cycles. However, at very low duty cycles, large deviations can be induced since only a few pulses are picked. Lower modulation frequencies can further improve the sensitivity at lower duty cycles, although this could come at the cost of imaging speed. To avoid intensity drifts between different pixels at low modulation frequencies, pixel dwell time might need to be carefully selected. However, phase-locking the function generator to the laser repetition could further improve the sensitivity values at low duty cycles.

The performance of PPCARS microscopes according to embodiments of the present disclosure can potentially be further improved in some ways. First, a very low duty cycle that can be achieved is 1% using 700 kHz and 300 kHz modulation frequencies. Further reducing the duty cycle could continue to boost the sensitivity at low modulation frequencies. Second, the efficiency of the AOM can potentially be further improved by using optimized crystal coating. Third, using an electro-optic modulator (EOM) that uses a higher rise time but does not shift angles at different wavelengths could also give better sensitivity enhancement at low duty cycles.

Typically, TPEF and SHG biological imaging prefer femtosecond (fs) lasers for excitation. With the significant sensitivity improvement accompanying embodiments of the present disclosure, picosecond (ps) excitation can achieve for both CARS imaging with high spectral resolution and TPEF and SHG imaging with good sensitivity. Embodiments of the present disclosure are not only suitable for ps-ps CARS, but are also applicable for fs-fs CARS, fs TPEF, three-photon fluorescence, sum frequency generation, and third harmonic generation. And, it is expected that this pulse picking technology will give better sensitivity enhancement for higher-order nonlinear optical processes.

An example of a PPCARS microscope according to embodiments of the present disclosure follows. FIG. 1 may be used as a reference. A dual-output 80-MHz femtosecond pulsed laser source (for example, InSight X3+, Spectra-Physics) is used for signal excitation. The 120-fs wavelength tunable output (680-1300 nm) is used as the pump beam and the 120-fs 1045 nm fixed-wavelength output is used as the Stokes beam. The beams are chirped using glass rods (for example, SF57, Lattice Electro Optics). One 150 mm rod is placed in the probe beam pathway and two 150 mm rods are used to chirp the combined beams. The optical beams are bent to double-pass the two chirping rods to increase the chirping. This 1+4 (Stokes+combined) configuration allows chirping of the pump beam to 3.4 µs and the Stokes beam to 1.8 µs before entering the microscope.

Hyperspectral CARS imaging is performed by scanning a 1D motorized delay stage (for example, X-LSM050A, Zaber Technologies) at 10 µm per step while collecting single-color CARS images at each delay position. The combined beams are then directed to an acousto-optic modulator (AOM, for example, 1250-C, Isomet) and modulated at different frequencies by a function generator (for example, DG1022Z, Rigol). The modulated $1^{st}$ order beams are directed to a 2D galvo scanner set (for example, GVS002, Thorlabs) and then into an upright microscope (for example, Olympus BX51). Either a 40×/0.8 NA (for example, LUMP-LFLN 40XW, Olympus) or a 60×/1.2 NA water immersion objective lens (for example, UPLSAPO 60X, Olympus) is used to focus the beams onto the sample. The FCARS signal is collected by a 1.4 NA oil-immersion condenser.

For FCARS imaging in the C—H region, the signal is directed through a 776 long-pass dichroic mirror (for example, FF776-Di01-25×36, Semrock) and then detected with a PMT (for example, H7422P-40, Hamamatsu) combined with a PMT amplifier (for example, PMT-4V3 amplifier, Advanced Research Instruments Corp).

For FCARS imaging in the fingerprint region, a combination of filters is used before a modified PMT (for example, PMT1001, Thorlabs) for signal acquisition, and the signals are also amplified by the PMT amplifier (for example, PMT-4V3 amplifier, Advanced Research Instruments Corp).

For epi-imaging, the signals are directed using a 776 nm long-pass dichroic mirror (for example, FF776-Di01-25×36, Semrock), separated using a 538 nm long-pass dichroic mirror (for example, FF536-FDi01-25×36, Semrock), and then detected with separate PMT.

For the FCARS and ECARS detections, 655/30 nm filters are used (for example, AT655/30m, Chroma Technology).

For epi-detected TPEF, two separate channels, including PMT2 with a 451/106 nm filter (for example, FF01-451/106-25, Semrock) and PMT3 with a 575/59 nm filter (for example, FF01-575/59-25, Semrock) are used to detect fluorescence signals in different ranges. 800 nm pulses may be used to excite the fluorescence beads, and both 800 nm and 1045 nm pulses may be used for tissue imaging.

For SHG signal detection, a 520/20 nm filter is used with PMT3. A 3D motorized translational stage (for example, H101, ProScan III, Prior Technology) is used to control sample and objective positions and perform automated large-area image acquisition and stitching, as well as 3D imaging.

Images are acquired by a data acquisition card (for example, PCIe-6363, National Instruments) and lab-written software based on LabVIEW. The original images were saved in .txt format and processed by, for example, ImageJ. Image contrast and brightness are adjusted for proper display. Pseudo-color maps are created by, for example, ImageJ functions. Intensity profiles are analyzed by, for example, ImageJ and plotted using, for example, Origin. Spectral phasor analysis is performed by a phasor plug-in. Gates for different compositions are manually selected for chemical separations. For SNR analysis, signals are selected from the sample areas and noises are chosen from the blank locations. For sensitivity analysis, to avoid PMT saturation, different input powers are used for different duty cycles. The intensities are calibrated using the pump and Stokes power values. The SNR increases shown in FIGS. 4A-7 may be derived by dividing the calibrated SNR at each duty cycle by the SNR from the 97% duty cycle. A 97% duty cycle may be used to mimic normal CARS imaging conditions since the function generator may be unable to generate 100% duty cycle square waves. TPEF and SHG SNR increases are analyzed similarly. Large-area mapping images are acquired on separate software written in, for example, LabVIEW to control the 2D translational sample stage for automated image stitching. 3D image acquisition is also performed using a lab-written program, for example, LabVIEW.

Phase retrieval of CARS spectra was performed using a lab-written script, for example, using MATLAB. The script was based on Kramers-Kronig relations and was utilized for removing the nonresonant background and obtaining Raman spectra from the hyperspectral CARS imaging of DMSO in $D_2O$ below 1% concentration, mixed PMMA and PS beads, and MIA PaCa-2 cells.

To further evaluate improvements achieved by embodiments of the present disclosure, the photo-perturbation to biological systems was evaluated using intact mouse tissue sections and by quantification of LD dynamics in live cells. It was demonstrated that in some embodiments where the duty cycle was reduced to 80 MHz, sensitivities were improved while reducing phototoxicity. The pulse picking method and apparatuses of the present disclosure can significantly reduce the duty cycle to 1.4%, corresponding to approximately 1 MHz repetition rate of ps lasers.

Some embodiments utilize duty cycles of 1.4-5%, which correspond to approximately 1-4 MHz repetition rates, for ps pulses, which appear to provide excellent imaging results. Still further embodiments utilize a high repetition rate (for example, approximately 80 MHz) for fs laser pulses. Moreover, the duty cycles can be flexibly controlled by the pulse picking methods disclosed herein.

In general, signal-to-noise ratios of greater than 10 are typically considered to be a good quality image.

Reference systems that may be used herein can refer generally to various directions (e.g., upper, lower, forward and rearward), which are merely offered to assist the reader in understanding the various embodiments of the disclosure and are not to be interpreted as limiting. Other reference systems may be used to describe various embodiments, such as referring to the direction of projectile movement as it exits the firearm as being up, down, rearward or any other direction.

To clarify the use of and to hereby provide notice to the public, the phrases "at least one of A, B, . . . and N" or "at least one of A, B, N, or combinations thereof" or "A, B, . . . and/or N" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. As one example, "A, B and/or C" indicates that all of the following are contemplated: "A alone," "B alone," "C alone," "A and B together," "A and C together," "B and C together," and "A, B and C together." If the order of the items matters, then the term "and/or" combines items that can be taken separately or together in any order. For example, "A, B and/or C" indicates that all of the following are contemplated: "A alone," "B alone," "C alone," "A and B together," "B and A together," "A and C together," "C and A together," "B and C together," "C and B together," "A, B and C together," "A, C and B together," "B, A and C together," "B, C and A together," "C, A and B together," and "C, B and A together."

While examples, one or more representative embodiments and specific forms of the disclosure have been illustrated and described in detail in the drawings and foregoing description, the same is to be considered as illustrative and not restrictive or limiting. The description of particular features in one embodiment does not imply that those particular features are necessarily limited to that one embodiment. Some or all of the features of one embodiment can be used or applied in combination with some or all of the features of other embodiments unless otherwise indicated. One or more exemplary embodiments have been shown and described, and all changes and modifications that come within the spirit of the disclosure are desired to be protected.

What is claimed is:

1. A pulse picking multimodal nonlinear optical microscope, comprising:
    one or more lasers configured to generate two or more laser beams;
    a dichroic mirror configured to receive and combine the two or more laser beams into a combined laser beam;
    an acousto-optic modulator configured to receive the combined laser beam, modulate the combined laser beam at different frequencies, and output a modulated laser beam; and
    a microscope configured to receive the modulated laser beam from the acousto-optic modulator and focus the modulated laser beam onto a sample;
    wherein the one or more lasers define a single femtosecond laser with synchronized dual outputs, further comprising:
    a chirping device configured to receive the combined laser beam and chirp the combined laser beam and output a combined picosecond laser beam, wherein the acousto-optic modulator is configured to receive the combined picosecond laser beam.

2. The pulse picking multimodal nonlinear optical microscope of claim 1, wherein the acousto-optic modulator is controlled by a function generator.

3. The pulse picking multimodal nonlinear optical microscope of claim 1, wherein the $1^{st}$ diffraction order of the modulated laser beam output from the acousto-optic modulator is separated from the $0^{th}$ diffraction order, and the microscope is configured to receive the $1^{st}$ diffraction order.

4. The pulse picking multimodal nonlinear optical microscope of claim 1, wherein the microscope is configured to perform coherent anti-Stokes Raman scattering microscopy.

5. The pulse picking multimodal nonlinear optical microscope of claim 1, wherein the microscope is configured to perform two-photon excited fluorescence microscopy.

6. The pulse picking multimodal nonlinear optical microscope of claim 1, wherein the combined laser beam is applied to the acousto-optic modulator at the Bragg angle error condition and the microscope collinearly combines the resulting spatially overlapped pump and Stokes beams at the first order diffraction of the acousto-optic modulator.

7. The pulse picking multimodal nonlinear optical microscope of claim 6, further comprising:
    a function generator connected to the acousto-optic modulator, wherein the combined beams are modulated at different frequencies by the function generator.

8. The pulse picking multimodal nonlinear optical microscope of claim 7, further comprising:
    a 2D galvanometer scanner; and
    a microscope, wherein the 2D galvanometer scanner receives the combined beam and directs the combined beam to the microscope, and the microscope focuses the beam onto a sample.

9. The pulse picking multimodal nonlinear optical microscope of claim 7, wherein the image quality is maintained or increased while the phototoxicity of the sample is decreased.

10. The pulse picking multimodal nonlinear optical microscope of claim 9, further comprising:
    a power supply, wherein the power supply delivers an average power from 2 mW to 30 mW and peak power from 50 W to 4000 W during imaging.

11. The pulse picking multimodal nonlinear optical microscope of claim 10, wherein the power supply delivers an average power of approximately 24 mW and peak power of approximately 3600 W during imaging.

12. The pulse picking multimodal nonlinear optical microscope of claim 1, wherein the microscope is a coherent Raman scattering microscope.

13. A method for obtaining an image of a tissue sample, comprising:
- generating two or more laser beams at different frequencies;
- shifting the polarization direction of the two or more laser beams;
- delaying at least one of the two or more laser beams;
- merging the two or more laser beams into a spatially overlapped laser beam;
- modulating the spatially combined laser beam at different frequencies;
- focusing the modulated laser beam onto a sample; and
- obtaining an image from the sample after said focusing;
- wherein said generating produces two or more pulsed laser beams with a femtosecond pulse rate, the method further comprising:
    - chirping the spatially overlapped laser beam to a spatially overlapped laser beam with a picosecond pulse rate.

14. The method for obtaining an image of a tissue sample of claim 13, wherein said focusing is accomplished with a microscope, the method further comprising:
- separating the $1^{st}$ diffraction order of the modulated spatially combined laser beam; and
- directing the $1^{st}$ diffraction order of the modulated spatially combined laser beam to the microscope.

15. The method for obtaining an image of a tissue sample of claim 13, wherein the two or more laser beams are pump and Stokes beams.

16. The method for obtaining an image of a tissue sample of claim 13, wherein said generating includes supplying a laser with an average power from 2 mW to 30 mW and peak power from 50 W to 4000 W.

17. The method for obtaining an image of a tissue sample of claim 13, wherein said generating includes supplying a laser with an average power of approximately 24 mW and peak power of approximately 3600 W.

18. A pulse picking multimodal nonlinear optical microscope, comprising:
- one or more lasers configured to generate two or more laser beams;
- a dichroic mirror configured to receive and combine the two or more laser beams into a combined laser beam;
- an acousto-optic modulator configured to receive the combined laser beam, modulate the combined laser beam at different frequencies, and output a modulated laser beam; and
- a microscope configured to receive the modulated laser beam from the acousto-optic modulator and focus the modulated laser beam onto a sample;
- wherein the combined laser beam is applied to the acousto-optic modulator at the Bragg angle error condition and the microscope collinearly combines the resulting spatially overlapped pump and Stokes beams at the first order diffraction of the acousto-optic modulator.

19. The pulse picking multimodal nonlinear optical microscope of claim 18, further comprising:
- a function generator connected to the acousto-optic modulator, wherein the combined beams are modulated at different frequencies by the function generator.

20. The pulse picking multimodal nonlinear optical microscope of claim 18, wherein the $1^{st}$ diffraction order of the modulated laser beam output from the acousto-optic modulator is separated from the $0^{th}$ diffraction order, and the microscope is configured to receive the $1^{st}$ diffraction order.

* * * * *